(12) United States Patent
Donde et al.

(10) Patent No.: US 7,427,685 B2
(45) Date of Patent: Sep. 23, 2008

(54) THERAPEUTIC SUBSTITUTED CYCLOPENTANES

(75) Inventors: Yariv Donde, Dana Point, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/553,143

(22) Filed: Oct. 26, 2006

(65) Prior Publication Data

US 2007/0129552 A1 Jun. 7, 2007

Related U.S. Application Data

(60) Provisional application No. 60/742,779, filed on Dec. 6, 2005.

(51) Int. Cl.
*C07D 333/38* (2006.01)
*C07C 63/00* (2006.01)
*C07C 69/76* (2006.01)

(52) U.S. Cl. .............................. 549/71; 562/405; 560/59

(58) Field of Classification Search ........................ None
See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen | |
| 5,902,726 A | 5/1999 | Kliewer et al. | |
| 6,437,146 B1 | 8/2002 | Hattori et al. | |
| 6,710,072 B2 | 3/2004 | Burk et al. | |
| 7,091,231 B2 * | 8/2006 | Donde et al. | 514/381 |
| 7,101,904 B2 * | 9/2006 | Donde et al. | 514/438 |
| 7,101,906 B2 * | 9/2006 | Donde et al. | 514/443 |
| 7,183,310 B2 * | 2/2007 | Donde et al. | 514/438 |
| 2006/0205800 A1 * | 9/2006 | Donde et al. | 514/381 |
| 2007/0112051 A1 * | 5/2007 | Donde et al. | 514/381 |

OTHER PUBLICATIONS

Baxter, et al., *Synthesis and Use of 7-Sbustituted Norbornadienes for the preparation of Prostagalandins and Prostanoids*, J. Chem Soc. Perkins Trans., 1986, p. 889.

Dragoli, et al., *Parallel Synthesis of Prostaglandfin E₁ Analogues*, J. Comb. Chem. 1999, 534-539, 1980.

Chourasia, M. K., Jain, S. K.,, *Pharmaceutical approaches to colon targeted drug delivery systems*, 2003, 33-66, J Pharm Pharmaceut Sci 6(1).

Mack Publishing Company, Remington's Pharmaceutical Sciences, 1980, 16th edition.

Reich, S. H., *Substituted Benzamide Inhibitors of Human Rhinovirus 3C Protease: Structure-Based Design, Synthesis, and Biological Evaluation*, 2000, 1670-1683.

Shareef, et al., *Colonic Drug Delivery: An Updated Review*, 2003, 161-186.

* cited by examiner

*Primary Examiner*—Yvonne Eyler
*Assistant Examiner*—Louisa Lao
(74) *Attorney, Agent, or Firm*—Allergan, Inc.; Martin Voet; Brent A. Johnson

(57) ABSTRACT

Therapeutic compounds according to one of the structures below are disclosed herein.

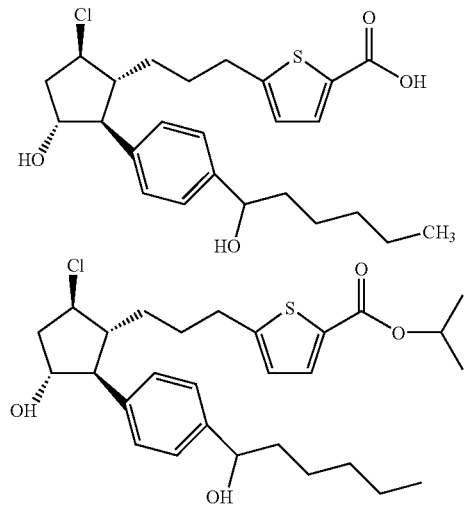

2 Claims, No Drawings

THERAPEUTIC SUBSTITUTED CYCLOPENTANES

CROSS REFERENCE TO RELATED APPLICATIONS

This application is based on, and claims the benefit of, U.S. Provisional Application No. 60/742,779, filed Dec. 6, 2005, and which is incorporated herein by reference.

BACKGROUND OF THE INVENTION

Description of the Related Art

Prostaglandin $EP_2$ selective agonists are useful for treating glaucoma, and are believed to have several medical uses, For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturiao, or the like."

U.S. Pat. No. 6,710,072 teaches the use of $EP_2$ agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

DESCRIPTION OF THE INVENTION

A compound comprising

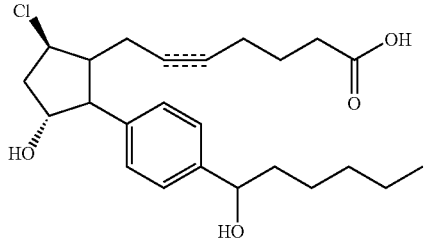

or a pharmaceutically acceptable salt or prodrug thereof, wherein a dashed line indicates the presence or absence of a bond, is disclosed herein.

As a dashed line indicates the presence or absence of a bond, the compounds shown below, or pharmaceutically acceptable salts or prodrugs thereof, are possible.

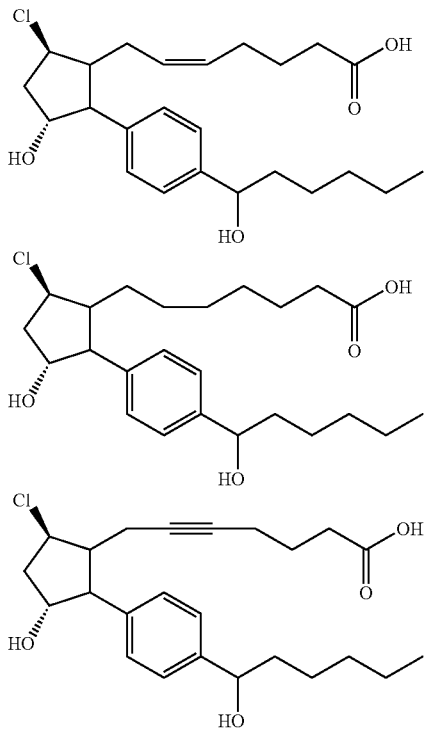

While not intending to limit the scope of the invention in any way, compounds having the stereochemistry indicated in the structures below, and pharmaceutically acceptable salts and prodrugs thereof, are specifically contemplated.

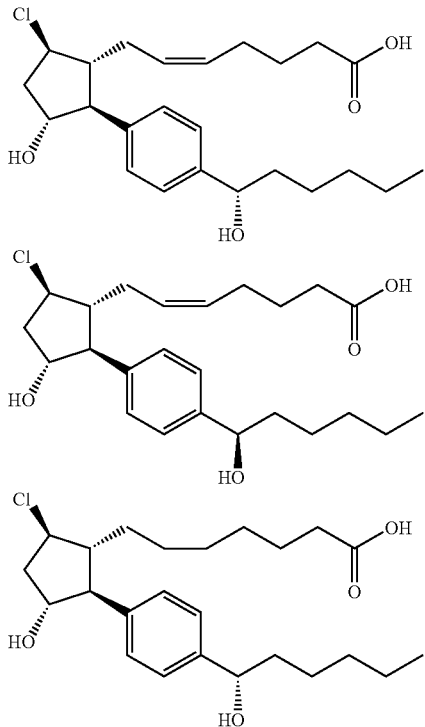

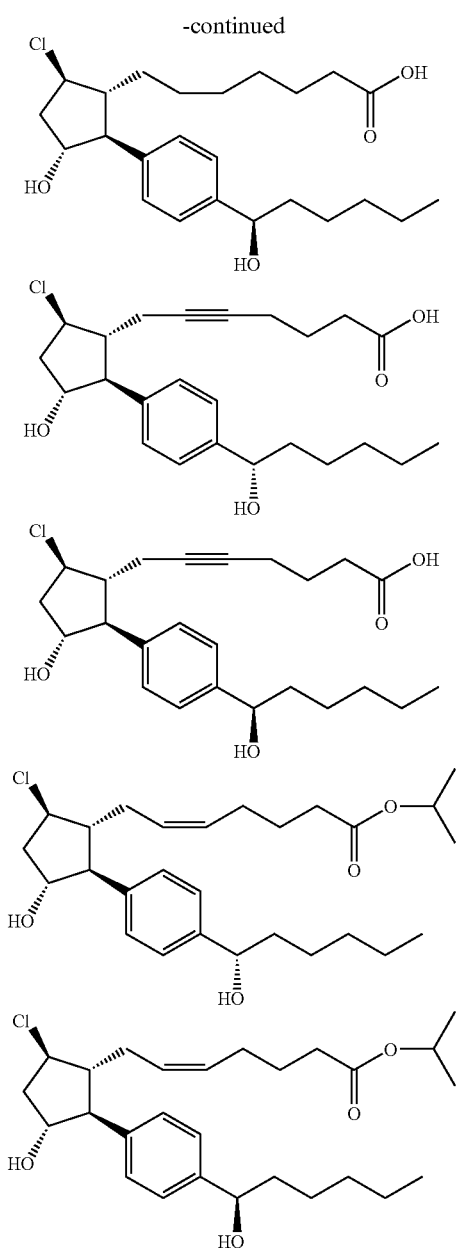

The compounds of disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_2$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc. A $C_{1-6}$ alkyl ester has an alkyl moiety of from 1 to 6 carbons directly attached to the oxygen of the ester.

The compounds below are of particular interest as prodrugs.

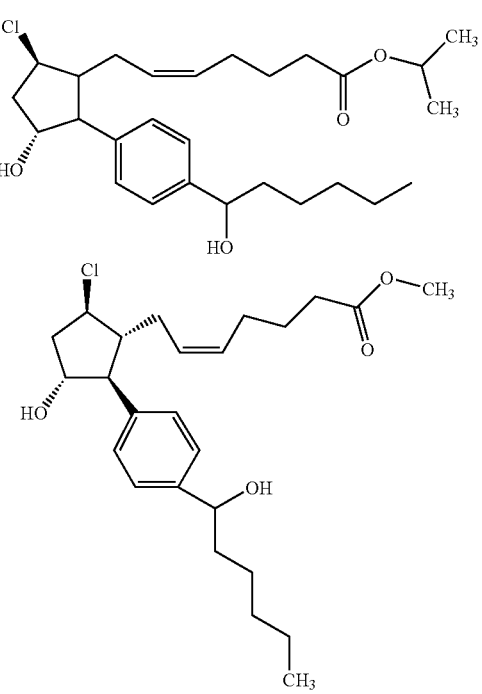

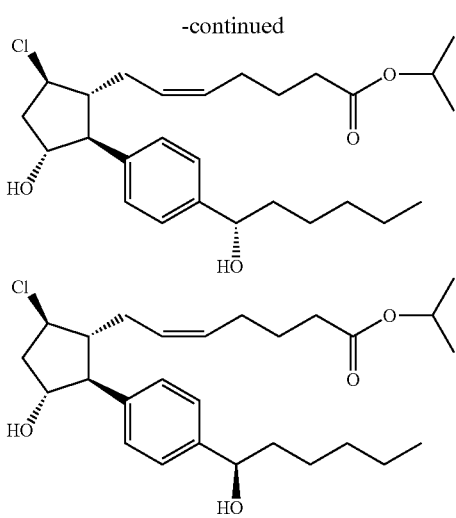

In another embodiment said ester prodrug is a $C_{1-6}$ alkyl ester of said compound.

The following compounds are also contemplated:

3-(3-{(1R,2S,3R,5R)-5-Chloro-3-hydroxy-2-[4-(1-hydroxy-hexyl)-phenyl]-cyclopentyl}-propyl)-benzoic acid (entry 1, table 1);

3-(3-{(1R,2S,3R,5R)-5-Chloro-3-hydroxy-2-[4-(1-hydroxy-hexyl)-phenyl]-cyclopentyl}-propyl)-benzoic acid ethyl ester;

5-(3-{(1R,2S,3R,5R)-5-Chloro-3-hydroxy-2-[4-(1-hydroxy-hexyl)-phenyl]-cyclopentyl}-propyl)-thiophene-2-carboxylic acid (entry 2, table 1);

5-(3-{(1R,2S,3R,5R)-5-Chloro-3-hydroxy-2-[4-(1-hydroxy-hexyl)-phenyl]-cyclopentyl}-propyl)-thiophene-2-carboxylic acid methyl ester;

5-(3-{(1R,2S,3R,5R)-5-Chloro-3-hydroxy-2-[4-(1-hydroxy-hexyl)-phenyl]-cyclopentyl}-propyl)-thiophene-2-carboxylic acid isopropyl ester;

3-(3-{(1R,2S,3R,5R)-5-Chloro-3-hydroxy-2-[4-(1-hydroxy-hexyl)-phenyl]-cyclopentylmethyl}-phenyl)-propionic acid (entry 3, table 1);

3-(3-{(1R,2S,3R,5R)-5-Chloro-3-hydroxy-2-[4-(1-hydroxy-hexyl)-phenyl]-cyclopentylmethyl}-phenyl)-propionic acid methyl ester;

3-[3-((1R,2S,3R,5R)-5-Chloro-3-hydroxy-2-{3-[hydroxy-(1-propyl-cyclobutyl)-methyl]-phenyl}-cyclopentylmethyl)-phenyl]-propionic acid (entry 4, table 1);

3-[3-((1R,2S,3R,5R)-5-Chloro-3-hydroxy-2-{3-[hydroxy-(1-propyl-cyclobutyl)-methyl]-phenyl}-cyclopentylmethyl)-phenyl]-propionic acid methyl ester;

2-(3-{(1R,2S,3R,5R)-5-Chloro-3-hydroxy-2-[4-(1-hydroxy-hexyl)-phenyl]-cyclopentyl}-propyl)-thiazole-5-carboxylic acid (entry 5, table 1);

2-(3-{(1R,2S,3R,5R)-5-Chloro-3-hydroxy-2-[4-(1-hydroxy-hexyl)-phenyl]-cyclopentyl}-propyl)-thiazole-5-carboxylic acid ethyl ester;

(Z)-7-{(1R,2S,3R,5R)-5-Fluoro-3-hydroxy-2-[4-(1-hydroxy-hexyl)-phenyl]-cyclopentyl}-hept-5-enoic acid (entry 8, table 1);

(Z)-7-{(1R,2S,3R,5R)-5-Fluoro-3-hydroxy-2-[4-(1-hydroxy-hexyl)-phenyl]-cyclopentyl}-hept-5-enoic acid methyl ester;

(Z)-7-{(1R,2S,3R,5S)-5-Chloro-3-hydroxy-2-[4-(1-hydroxy-hexyl)-phenyl]-cyclopentyl}-hept-5-enoic acid (entry 9, table 1);

(Z)-7-{(1R,2S,3R,5S)-5-Chloro-3-hydroxy-2-[4-(1-hydroxy-hexyl)-phenyl]-cyclopentyl}-hept-5-enoic acid methyl ester;

(Z)-7-{(1R,2S,3R,5R)-5-Chloro-3-hydroxy-2-[4-(1-hydroxy-hexyl)-phenyl]-cyclopentyl}-hept-5-enoic acid methyl ester (entry 10, table 1);

(Z)-7-{(1R,2S,3R,5R)-5-Chloro-3-hydroxy-2-[4-(1-hydroxy-hexyl)-phenyl]-cyclopentyl}-hept-5-enoic acid (entry 11-13, table 1);

(Z)-7-{(1R,2S,3R,5R)-5-Chloro-3-hydroxy-2-[4-(1-hydroxy-hexyl)-phenyl]-cyclopentyl}-hept-5-enoic acid isopropyl ester;

7-{(1R,2S,3R,5R)-5-Chloro-3-hydroxy-2-[4-(1-hydroxy-hexyl)-phenyl]-cyclopentyl}-heptanoic acid (entry 14, table 1);

7-{(1R,2S,3R,5R)-5-Chloro-3-hydroxy-2-[4-(1-hydroxy-hexyl)-phenyl]-cyclopentyl}-heptanoic acid methyl ester;

(Z)-7-{(1R,2S,3R,5R)-5-Chloro-2-[4-(3-cyclohexyl-1-hydroxy-propyl)-phenyl]-3-hydroxy-cyclopentyl}-hept-5-enoic acid (entry 15, table 1);

(Z)-7-{(1R,2S,3R,5R)-5-Chloro-2-[4-(3-cyclohexyl-1-hydroxy-propyl)-phenyl]-3-hydroxy-cyclopentyl}-hept-5-enoic acid methyl ester;

7-{(1R,2S,3R,5R)-5-Chloro-2-[4-(3-cyclohexyl-1-hydroxy-propyl)-phenyl]-3-hydroxy-cyclopentyl}-heptanoic acid (entry 16, table 1);

7-{(1R,2S,3R,5R)-5-Chloro-2-[4-(3-cyclohexyl-1-hydroxy-propyl)-phenyl]-3-hydroxy-cyclopentyl}-heptanoic acid methyl ester;

(Z)-7-{(1R,2S,3R,5R)-5-Chloro-2-[4-(2-cyclohexyl-1-hydroxy-ethyl)-phenyl]-3-hydroxy-cyclopentyl}-hept-5-enoic acid (entry 17, table 1);

(Z)-7-{(1R,2S,3R,5R)-5-Chloro-2-[4-(2-cyclohexyl-1-hydroxy-ethyl)-phenyl]-3-hydroxy-cyclopentyl}-hept-5-enoic acid methyl ester;

7-{(1R,2S,3R,5R)-5-Chloro-2-[4-(2-cyclohexyl-1-hydroxy-ethyl)-phenyl]-3-hydroxy-cyclopentyl}-heptanoic acid (entry 18, table 1);

7-{(1R,2S,3R,5R)-5-Chloro-2-[4-(2-cyclohexyl-1-hydroxy-ethyl)-phenyl]-3-hydroxy-cyclopentyl}-heptanoic acid methyl ester;

(Z)-7-{(1R,2S,3R,5R)-5-Chloro-3-hydroxy-2-[4-(1-hydroxy-5,5-dimethyl-hexyl)-phenyl]-cyclopentyl}-hept-5-enoic acid methyl ester;

(Z)-7-{(1R,2S,3R,5R)-5-Chloro-3-hydroxy-2-[4-(1-hydroxy-5,5-dimethyl-hexyl)-phenyl]-cyclopentyl}-hept-5-enoic acid (entry 19, table 1);

7-{(1R,2S,3R,5R)-5-Chloro-3-hydroxy-2-[4-(1-hydroxy-5,5-dimethyl-hexyl)-phenyl]-cyclopentyl}-heptanoic acid methyl ester;

7-{(1R,2S,3R,5R)-5-Chloro-3-hydroxy-2-[4-(1-hydroxy-5,5-dimethyl-hexyl)-phenyl]-cyclopentyl}-heptanoic acid (entry 20, table 1);

(Z)-7-{(1R,2S,3R,5R)-5-Chloro-3-hydroxy-2-[4-(1-hydroxy-2-phenyl-ethyl)-phenyl]-cyclopentyl}-hept-5-enoic acid methyl ester;

(Z)-7-{(1R,2S,3R,5R)-5-Chloro-3-hydroxy-2-[4-(1-hydroxy-2-phenyl-ethyl)-phenyl]-cyclopentyl}-hept-5-enoic acid isopropyl ester;

(Z)-7-{(1R,2S,3R,5R)-5-Chloro-3-hydroxy-2-[4-(1-hydroxy-2-phenyl-ethyl)-phenyl]-cyclopentyl}-hept-5-enoic acid (entry 21, table 1);

7-{(1R,2S,3R,5R)-5-Chloro-3-hydroxy-2-[4-(1-hydroxy-2-phenyl-ethyl)-phenyl]-cyclopentyl}-heptanoic acid methyl ester;

7-{(1R,2S,3R,5R)-5-Chloro-3-hydroxy-2-[4-(1-hydroxy-2-phenyl-ethyl)-phenyl]-cyclopentyl}-heptanoic acid (entry 22, table 1);

(Z)-7-{(1R,2S,3R,5R)-5-Chloro-3-hydroxy-2-[4-(1-hydroxy-3-phenyl-propyl)-phenyl]-cyclopentyl}-hept-5-enoic acid methyl ester;

(Z)-7-{(1R,2S,3R,5R)-5-Chloro-3-hydroxy-2-[4-(1-hydroxy-3-phenyl-propyl)-phenyl]-cyclopentyl}-hept-5-enoic acid (entry 23, table 1);

7-{(1R,2S,3R,5R)-5-Chloro-3-hydroxy-2-[4-(1-hydroxy-3-phenyl-propyl)-phenyl]-cyclopentyl}-heptanoic acid methyl ester;

7-{(1R,2S,3R,5R)-5-Chloro-3-hydroxy-2-[4-(1-hydroxy-3-phenyl-propyl)-phenyl]-cyclopentyl}-heptanoic acid (entry 24, table 1);

(Z)-7-{(1R,2S,3R,5R)-5-Chloro-3-hydroxy-2-[4-(1-hydroxy-heptyl)-phenyl]-cyclopentyl}-hept-5-enoic acid methyl ester;

(Z)-7-{(1R,2S,3R,5R)-5-Chloro-3-hydroxy-2-[4-(1-hydroxy-heptyl)-phenyl]-cyclopentyl}-hept-5-enoic acid (entry 25, table 1);

(Z)-7-{(1R,2S,3R,5R)-5-Chloro-3-hydroxy-2-[4-(1-hydroxy-butyl)-phenyl]-cyclopentyl}-hept-5-enoic acid methyl ester;

(Z)-7-{(1R,2S,3R,5R)-5-Chloro-3-hydroxy-2-[4-(1-hydroxy-butyl)-phenyl]-cyclopentyl}-hept-5-enoic acid (entry 26, table 1);

(Z)-7-{(1R,2S,3R,5R)-5-Chloro-3-hydroxy-2-[4-(1-hydroxy-butyl)-phenyl]-cyclopentyl}-hept-5-enoic acid isopropyl ester;

(Z)-7-{(1R,2S,3R,5R)-5-Chloro-3-hydroxy-2-[4-(1-hydroxy-pentyl)-phenyl]-cyclopentyl}-hept-5-enoic acid methyl ester;

(Z)-7-{(1R,2S,3R,5R)-5-Chloro-3-hydroxy-2-[4-(1-hydroxy-pentyl)-phenyl]-cyclopentyl}-hept-5-enoic acid (entry 27, table 1);

(Z)-7-{(1R,2S,3R,5R)-5-Chloro-3-hydroxy-2-[4-(hydroxy-phenyl-methyl)-phenyl]-cyclopentyl}-hept-5-enoic acid methyl ester;

(Z)-7-{(1R,2S,3R,5R)-5-Chloro-3-hydroxy-2-[4-(hydroxy-phenyl-methyl)-phenyl]-cyclopentyl}-hept-5-enoic acid (entry 28, table 1);

(Z)-7-{(1R,2S,3R,5R)-5-Chloro-3-hydroxy-2-[3-(1-hydroxy-hexyl)-phenyl]-cyclopentyl}-hept-5-enoic acid methyl ester;

(Z)-7-{(1R,2S,3R,5R)-5-Chloro-3-hydroxy-2-[3-(1-hydroxy-hexyl)-phenyl]-cyclopentyl}-hept-5-enoic acid (entry 29, table 1);

(Z)-7-{(1R,2S,3R,5R)-5-Chloro-3-hydroxy-2-[3-(1-hydroxy-pentyl)-phenyl]-cyclopentyl}-hept-5-enoic acid methyl ester;

(Z)-7-{(1R,2S,3R,5R)-5-Chloro-3-hydroxy-2-[3-(1-hydroxy-pentyl)-phenyl]-cyclopentyl}-hept-5-enoic acid (entry 30, table 1);

(Z)-7-{(1R,2S,3R,5R)-5-Chloro-3-hydroxy-2-[4-(2-hydroxy-1,1-dimethyl-heptyl)-phenyl]-cyclopentyl}-hept-5-enoic acid methyl ester;

(Z)-7-{(1R,2S,3R,5R)-5-Chloro-3-hydroxy-2-[4-(2-hydroxy-1,1-dimethyl-heptyl)-phenyl]-cyclopentyl}-hept-5-enoic acid (entry 31, table 1);

(Z)-7-{(1R,2S,3R,5R)-5-Chloro-3-hydroxy-2-[4-(2-hydroxy-1,1-dimethyl-hexyl)-phenyl]-cyclopentyl}-hept-5-enoic acid methyl ester;

(Z)-7-{(1R,2S,3R,5R)-5-Chloro-3-hydroxy-2-[4-(2-hydroxy-1,1-dimethyl-hexyl)-phenyl]-cyclopentyl}-hept-5-enoic acid (entry 32, table 1);

(Z)-7-[(1R,2S,3R,5R)-5-Chloro-2-(4-hexyl-phenyl)-3-hydroxy-cyclopentyl]-hept-5-enoic acid (entry 33, table 1);

(Z)-7-[(1R,2S,3R,5R)-5-Chloro-2-(4-hexyl-phenyl)-3-hydroxy-cyclopentyl]-hept-5-enoic acid methyl ester;

(Z)-7-[(1R,2S,3R,5R)-5-Chloro-2-(4-hexyl-phenyl)-3-hydroxy-cyclopentyl]-hept-5-enoic acid isopropyl ester; and (Z)-7-{(1R,2S,3 S,5R)-5-Chloro-3-hydroxy-2-[4-(1-hydroxy-hexyl)-phenyl]-cyclopentyl}-hept-5-enoic acid (211217).

All compounds disclosed in Table 1 and Table 2, as well as any pharmaceutically acceptable salt, or any prodrug thereof, are specifically contemplated herein.

In addition to any embodiments otherwise disclose herein, the following embodiments are specifically contemplated.

One embodiment is use of any compound disclosed herein, including those disclosed in Tables 1 and 2, in the manufacture of a medicament for the treatment of glaucoma or ocular hypertension.

Another embodiment is use of any compound disclosed herein, including those disclosed in Tables 1 and 2, in the manufacture of a medicament for the treatment of an inflammatory bowel disease.

Another embodiment is a method comprising administering any compound disclosed herein, including those disclosed in Tables 1 and 2, topically to an eye of a mammal for the treatment of glaucoma or ocular hypertension.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds may be in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

The compounds disclosed herein are also useful in combination with other drugs useful for the treatment of glaucoma or other conditions.

For the treatment of glaucoma, combination treatment with the following classes of drugs are contemplated:

β-Blockers (or β-adrenergic antagonists) including carteolol, levobunolol, metiparanolol, timolol hemihydrate, timolol maleate, β1-selective antagonists such as betaxolol, and the like, or pharmaceutically acceptable salts or prodrugs thereof;

Adrenergic Agonists including non-selective adrenergic agonists such as epinephrine borate, epinephrine hydrochloride, and dipivefrin, and the like, or pharmaceutically acceptable salts or prodrugs thereof, and $\alpha_2$-selective adrenergic agonists such as apraclonidine, brimonidine, and the like, or pharmaceutically acceptable salts or prodrugs thereof, Carbonic Anhydrase Inhibitors including acetazolamide, dichlorphenamide, methazolamide, brinzolamide, dorzolamide, and the like, or pharmaceutically acceptable salts or prodrugs thereof;

Cholinergic Agonists including direct acting cholinergic agonists such as carbachol, pilocarpine hydrochloride, pilocarbine nitrate, pilocarpine, and the like, or pharmaceutically acceptable salts or prodrugs thereof;

chlolinesterase inhibitors such as demecarium, echothiophate, physostigmine, and the like, or pharmaceutically acceptable salts or prodrugs thereof;

Glutamate Antagonists and other neuroprotective agents such as $Ca^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, bamidipine, verapamil, lidoflazine, prenylamine lactate, amiloride, and the like, or pharmaceutically acceptable salts or prodrugs thereof, Prostamides such as bimatoprost, or pharmaceutically acceptable salts or prodrugs thereof, and Prostaglandins including travoprost, UFO-21, chloprostenol, fluprostenol, 13,14-dihydro-chloprostenol, isopropyl unoprostone, latanoprost and the like.

Cannabinoids including CB1 agonists such as WIN-55212-2 and CP-55940 and the like, or pharmaceutically acceptable salts or prodrugs thereof.

For treatment of diseases affecting the eye including glaucoma, these compounds can be administered topically, periocularly, intraocularly, or by any other effective means known in the art.

These compounds can also be used to treat or prevent conditions affecting the posterior part of the eye include maculopathies/retinal degeneration such as non-exudative age related macular degeneration (ARMD), exudative age related macular degeneration (ARMD), choroidal neovascularization, diabetic retinopathy, acute macular neuroretinopathy, central serous chorioretinopathy, cystoid macular edema, and diabetic macular edema; uveitis/retinitis/choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vasuclar diseases/exudative diseases such as retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis. Preferably, the disease or condition is retinitis pigmentosa, proliferative vitreal retinopathy (PVR), age-related macular degeneration (ARMD), diabetic retinopathy, diabetic macular edema, retinal detachment, retinal tear, uveitis, or cytomegalovirus retinitis.

These compounds are also useful in treating asthma.

EXAMPLE 1

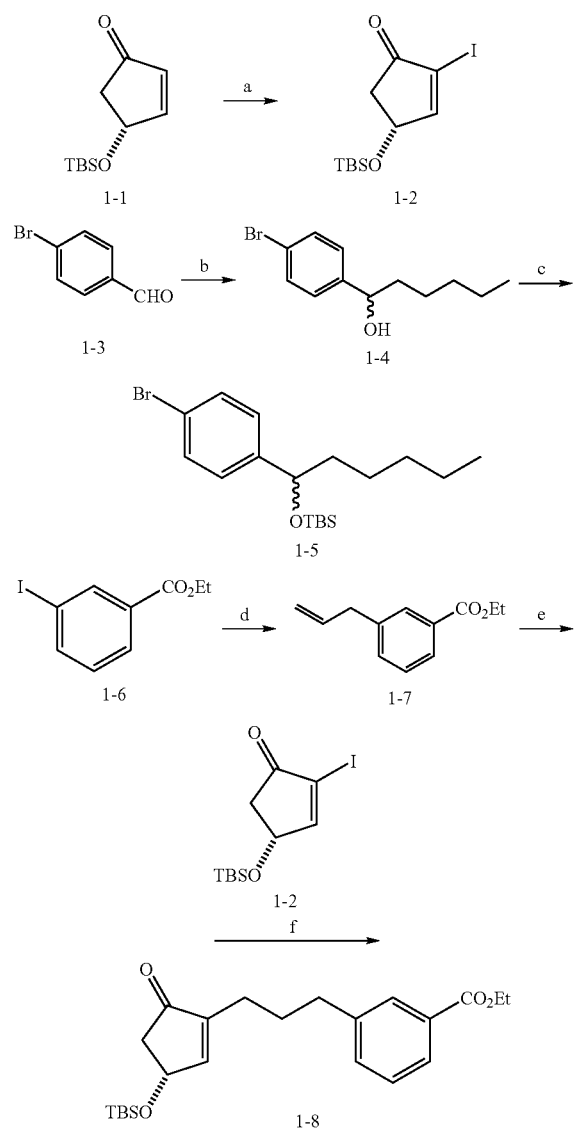

Scheme 1

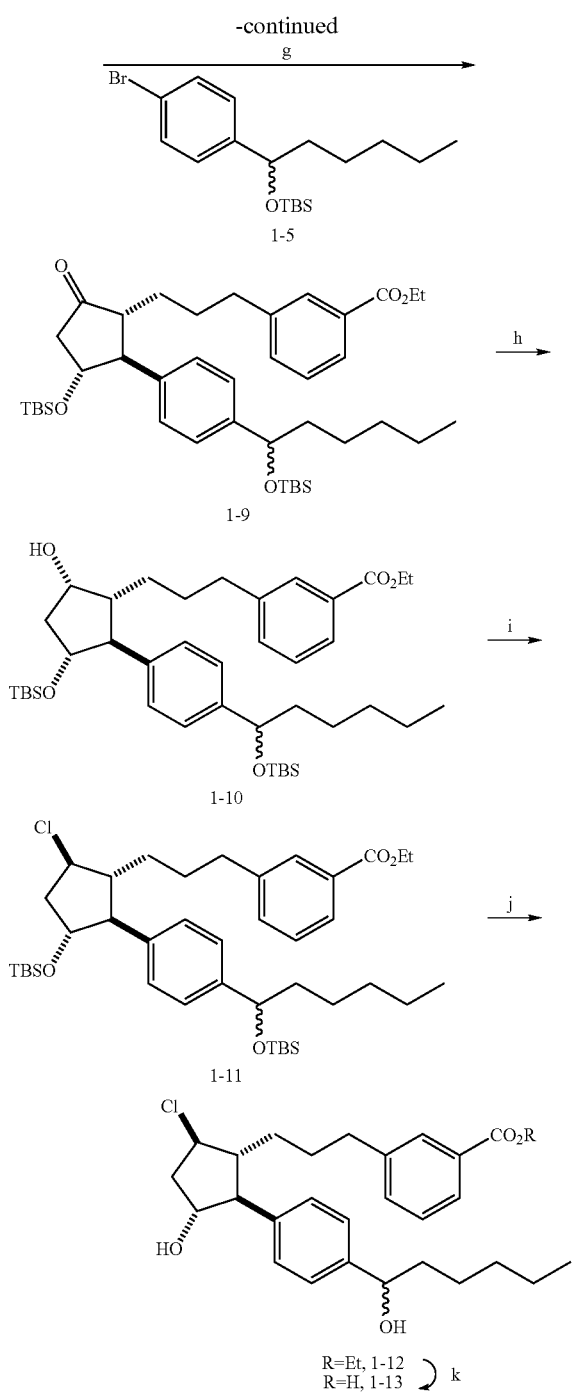

(a) I₂, pyridine, CH₂Cl₂; (b) n-pentylMgBr; (c) TBSOTf, 2,6-lutidine, CH₂Cl₂; (d) i-PrMgCl; cat. CuCN, allylbromide; (e) 9-BBN; (f) PdCl₂(dppf), K₃PO₄, DMF; (g) t-BuLi; 2-ThienylCuCNLi; (h) L-selectride; (i) MsCl, TEA; TBAC 40 °C. (j) HF·pyridine 0 °C.; (k) 1 M LiOH, THF.

(R)-4-(tert-Butyl-dimethyl-silanyloxy)-2-iodo-cyclopent-2-enone (1-2). A procedure similar to the one described in A. G. Myers and P. S. Dragovich *J. Am. Chem. Soc.* 1993, 115, 7021 was followed. A 0° C. solution of enone 1-1 (3.163 g, 14.9 mmol,Evotec OAI, 151 Milton Park, Abington, Oxon, OX 14 4SD, UK) and pyridine (5 mL) in dichloromethane (5 mL) was treated with a solution of I₂ (6.511 g, 25.7 mmol) in pyridine (12 mL)/dichloromethane (12 mL). The reaction was allowed to warm to room temperature and after 2 h, 1 M HCl (60 mL) was added.

The resulting mixture was poured into 100 mL 1 M HCl and then was extracted with dichloromethane (3×60 mL). The combined dichloromethane solution was washed with saturated NaHSO₃ solution and with brine and then was dried (Na₂SO₄), filtered and evaporated. Purification by flash chromatography on silica gel (5% ethyl acetate/hexanes) gave the title compound (4.600 g, 91%).

1-(4-Bromo-phenyl)-hexan-1-ol (1-4). n-PentylMgBr (29 mL, 58 mmol, 2 M/ether) was added to a 0° C. solution of 4-bromobenzaldehyde (9.953 g, 54 mmol) in THF (100 mL). After 1 h, the reaction was quenched by addition of 200 mL saturated ammonium chloride solution. The resulting mixture was extracted with ethyl acetate (3×100 mL) and the combined ethyl acetate solution was dried (Na2SO4), filtered and evaporated. Purification of the residue by flash chromatography on silica gel gave 1-4 (10.501 g, 76%).

[1-(4-Bromo-phenyl)-hexyloxy]-tert-butyl-dimethyl-silane (1-5). TBSOTf (2.9 mL, 12.6 mmol) was added to an ice-cold solution of 1-4 (3.017 g, 11.7 mmol) and 2,6-lutidine (1.6 mL, 13.7 mmol) in dichloromethane (30 mL). The reaction was stirred for 2 h at room temperature and then 100 mL saturated sodium bicarbonate solution was added. The resulting mixture was extracted with dichloromethane (30 mL) and the dichloromethane layer was washed with 1 M HCl (2×50 mL) and brine (50 mL). The dichloromethane solution was then dried (MgSO₄), filtered and evaporated. Purification of the residue by flash chromatography on silica gel (hexanes) gave 1-5 (3.843 g, 88%).

3-Allyl-benzoic acid ethyl ester (1-7). A −45° C. solution of ethyl 3-iodobenzoate (2.434 g, 8.8 mmol) in 40 mL THF was treated with i-PrMgCl (4.8 mL, 9.6 mmol, 2 M/ether). After 1 h, allyl bromide (1.6 mL, 18.9 mmol) was added followed by CuCN (79 mg, 0.88 mmol). The reaction was stirred for 1 h and then was quenched by addition of 50 mL saturated NH₄Cl solution. Water (30 mL) was added and the resulting mixture was extracted with ethyl acetate (3×50 mL). The combined ethyl acetate solution was dried (MgSO₄), filtered and evaporated. Purification by flash chromatography on silica gel (5% ethyl acetate/hexanes→10%) gave the title compound (1.145 g, 68%).

3-{3-[(R)-3-(tert-Butyl-dimethyl-silanyloxy)-5-oxo-cyclopent-1-enyl]-propyl}-benzoic acid ethyl ester (1-8). A solution of 1-7 (303 mg, 1.6 mmol) in 0.5 mL THF was added to a solution of 9-BBN dimer (393 mg, 1.6 mmol) in 6 mL THF. After 4 h, 0.1 mL H₂O was added. The solution was stirred for 20 min. and then was cannula transferred to a mixture of PdCl₂(dppf) (78 mg, 0.11 mmol) and 1-2 (387 mg, 2.0 mmol) in DMF (3.2 mL). K₃PO₄ (0.7 mL, 2.1 mmol, 3 M) was added and the dark solution was stirred for 1.25 h. The solution was then poured into 50 mL brine and the resulting mixture was extracted with ethyl acetate (2×30 mL). The combined ethyl acetate solution was dried (MgSO₄), filtered and evaporated. Purification by flash chromatography on silica gel gave 292 mg (46%) of enone 1-8.

1-8→→3-(3-{(1R,2S,3R,5R)-5-Chloro-3-hydroxy-2-[4-(1-hydroxy-hexyl)-phenyl]-cyclopentyl}-propyl)-benzoic acid (1-13). The sequence leading to 1-13 was completed as shown in scheme 1 and as described in U.S. patent application Ser. No. 11/009,298, filed on Dec. 10, 2004 (now U.S. Pat. No. 7,091,231 issued Aug. 15, 2006), expressly incorporated by reference herein, FIGS. 5,6.

5-(3-{(1R,2S,3R,5R)-5-Chloro-3-hydroxy-2-[4-(1-hydroxy-hexyl)-phenyl]-cyclopentyl}-propyl)-thiophene-2-carboxylic acid methyl ester. The title compound was prepared using an analogous procedure to that described for 1-12, starting with 5-Bromo-thiophene-2-carboxylic acid methyl ester, which was prepared from 5-Bromo-thiophene-2-carboxylic acid as follows: Acetyl chloride (6.87 mL, 96.6 mmol) was added to a solution of 5-Bromo-thiophene-2-carboxylic acid (4.0 g, 19.3 mmol) in methanol (30 mL). The reaction was allowed to stir overnight and then was heated to reflux for 1.5 h. The reaction was allowed to cool to room temperature and then was evaporated. The residue was treated with 120 mL saturated sodium bicarbonate solution and the resulting mixture was extracted with dichloromethane (3×100 mL). The combined dichloromethane solution was dried ($Na_2SO_4$), filtered and evaporated to give 3.57 g (84%) of 5-Bromo-thiophene-2-carboxylic acid methyl ester.

5-(3-{(1R,2S,3R,5R)-5-Chloro-3-hydroxy-2-[4-(1-hydroxy-hexyl)-phenyl]-cyclopentyl}-propyl)-thiophene-2-carboxylic acid (entry 2, table 1). The title compound was prepared by hydrolysis of the methyl ester using the rabbit liver esterase procedure described in U.S. patent application Ser. No. 11/009,298, filed on Dec. 10, 2004 (now U.S. Pat. No. 7,091,231 issued Aug. 15, 2006).

5-(3-{(1R,2S,3R,5R)-5-Chloro-3-hydroxy-2-[4-(1-hydroxy-hexyl)-phenyl]-cyclopentyl}-propyl)-thiophene-2-carboxylic acid isopropyl ester. The title compound was prepared from the corresponding acid using the standard procedure described in U.S. patent application Ser. No. 11/009,298, filed on Dec. 10, 2004 (now U.S. Pat. No. 7,091,231 issued Aug. 15, 2006).

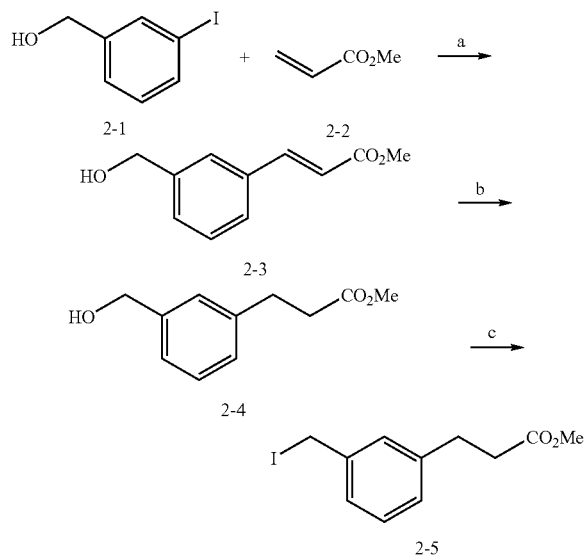

Scheme 2

(a) Pd(OAc)2, Et3N CH3CN 100 °C.; (b) H2, (Ph3P)3RhCl, EtOH; (c) Ph3P, I2, imidazole, ClCH2CH2Cl.

(E)-3-(3-Hydroxymethyl-phenyl)-acrylic acid methyl ester (2-3). The procedure described in Reich, S. H. et. al. *J. Med. Chem.* 2000, 43, 1670 was followed. $Pd(OAc)_2$ (8.2 mg, 0.037 mmol) and triethylamine (0.360 mL, 2.58 mmol) were added to a solution of 3-iodobenzyl alcohol 2-1 (0.27 mL, 2.13 mmol) and methyl acrylate 2-2 (0.220 mL, 2.44 mmol) in $CH_3CN$ (4.5 mL). The reaction vessel was sealed with a Teflon screw-cap and was heated at 100° C. for 5 h. At this time, the reaction was allowed to cool to room temperature and the tube was charged with 0.22 mL more of methyl acrylate, 11.7 mg $Pd(OAc)_2$ and 0.360 mL triethylamine. The reaction was heated at 100° C. overnight and then 10 mL saturated ammonium chloride solution was added. The resulting mixture was extracted with dichloromethane (3×40 mL) and the combined dichloromethane solution was dried ($Na_2SO_4$), filtered and evaporated. Purification by flash chromatography on silica gel (30% ethyl acetate/hexanes) gave 395 mg (97%) of 2-3.

3-(3-Hydroxymethyl-phenyl)-propionic acid methyl ester (2-4). $(Ph_3P)_3RhCl$ (11.5 mg, 0.012 mmol) was added to a solution of 2-3 (25 mg, 0.13 mmol) in 0.400 mL ethanol. The reaction was stirred under 1 atm $H_2$ balloon for 20 h and then was filtered through Celite. Evaporation to dryness and purification by flash chromatography on silica gel (30% ethyl acetate/hexanes) gave 2-4 (21 mg, 82%).

3-(3-Iodomethyl-phenyl)-propionic acid methyl ester (2-5). A mixture of $Ph_3P$ (36 mg, 0.14 mmol), $I_2$ (41 mg, 0.16 mmol) and imidazole (10.5 mg, 0.15 mmol) in 0.40 mL 1,2-dichloroethane was stirred for 15 min. and then a solution of 2-4 (20.5 mg, 0.11 mmol) in 0.1 mL 1,2-dichloroethane was added by cannula. The resulting mixture was stirred for 1 h and then was filtered through basic alumina, washing with ethyl acetate. The filtrate was evaporated and the residue was purified by flash chromatography on silica gel to give 2-5 (26 mg, 81%).

3-[3-((1R,2S,3R)-3-(tert-Butyl-dimethyl-silanyloxy)-2-{4-[1-(tert-butyl-dimethyl-silanyloxy)-hexyl]-phenyl}-5-oxo-cyclopentylmethyl)-phenyl]-propionic acid methyl ester (3-1). A −78° C. solution of aryl bromide 1-5 (759 mg, 2.0 mmol) in THF (3 mL) was treated with tert-butyllithium (2.6 mL, 4.4 mmol, 1.7 M/pentane). After 30 min., $Me_2Zn$ (1.1 mL, 2.2 mmol, 2 M/toluene) was added and the resulting solution was stirred for 15 min. at 0° C. and then was recooled to −78° C. A solution of enone 1-1 (319 mg, 1.5 mmol, Evotec OAI, 151 Milton Park, Abington, Oxon, OX 14 4SD, UK) in 1.7 mL THF was added by syringe pump over 1 h. The resulting mixture was stirred at −78° C. for 2 h, and then HMPA (2.2 mL, 12.6 mmol) was added followed by a solution of 2-5 (2.641 g, 8.7 mmol) in THF (1.6 mL). The reaction was stirred overnight at −40° C. and then was quenched by addition of 40 mL saturated ammonium chloride solution. A little water was added to dissolve the solids and the resulting mixture was extracted with ethyl acetate (3×30 mL). The combined ethyl acetate solution was dried ($MgSO_4$), filtered and evaporated. Purification by flash chromatography on silica gel (10% ethyl acetate/hexanes) gave the title ketone contaminated with ca. 35% of benzyl iodide 2-5 (438 mg).

Scheme 3

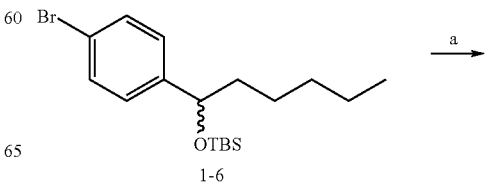

1-6

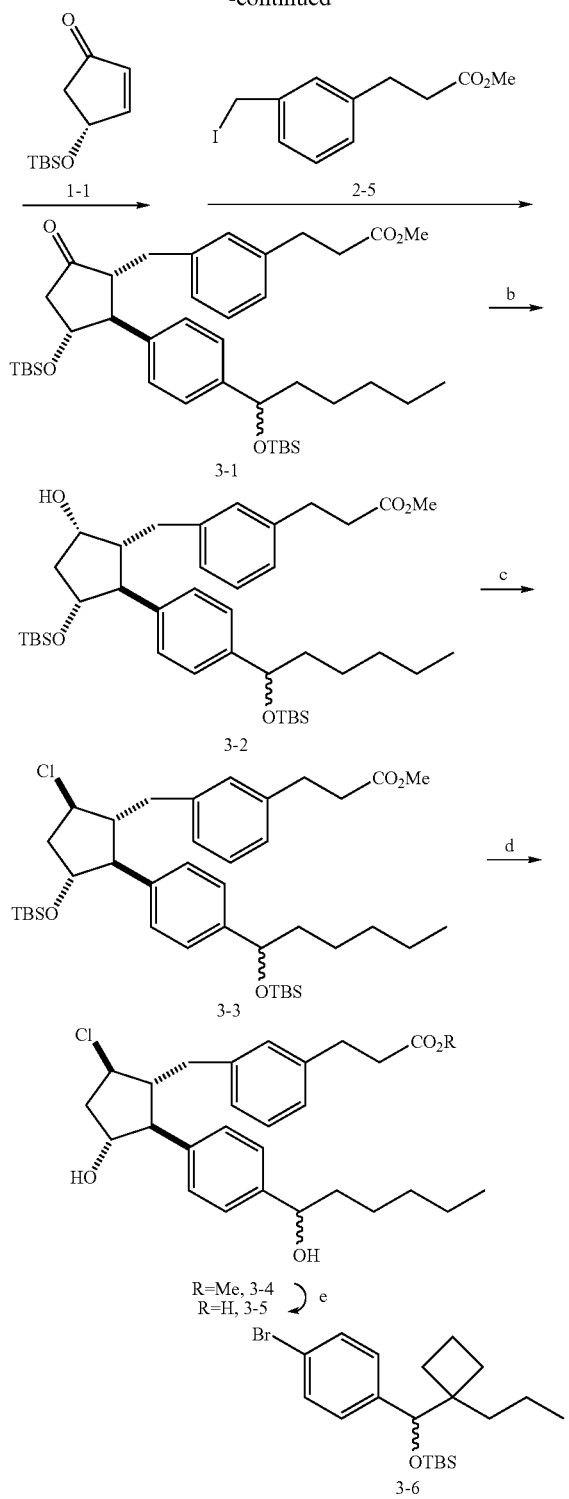

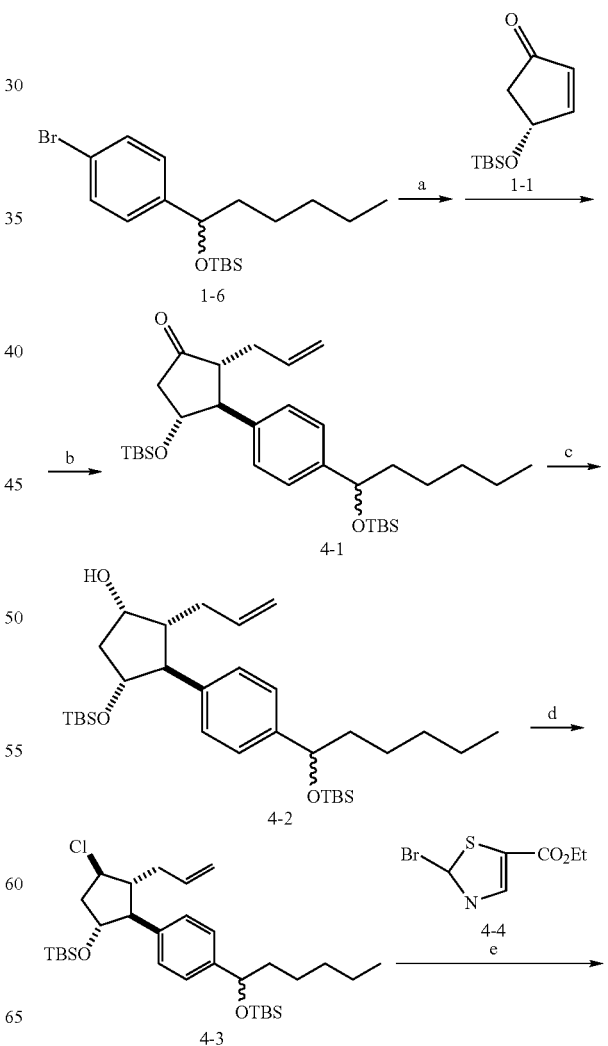

(a) t-BuLi; Me₂Zn; (b) L-selectride; (c) MsCl, TEA; TBAC 40 °C.; (d) HF·pyridine; (e) aq. LiOH.

3-[3-((1R,2S,3R,5S)-3-(tert-Butyl-dimethyl-silanyloxy)-2-{4-[1-(tert-butyl-dimethyl-silanyloxy)-hexyl]-phenyl}-5-hydroxy-cyclopentylmethyl)-phenyl]-propionic acid methyl ester (3-2). The standard L-selectride procedure described in U.S. patent application Ser. No. 11/009,298, filed on Dec. 10, 2004 (now U.S. Pat. No. 7,091,231 issued Aug. 15, 2006) was used, which gave 224 mg (22% from enone 1-1) of pure 3-2.

3-2→→3-(3-{(1R,2S,3R,5R)-5-Chloro-3-hydroxy-2-[4-(1-hydroxy-hexyl)-phenyl]-cyclopentylmethyl}-phenyl)-propionic acid (3-5). The sequence was completed as shown in scheme 3 using the standard procedures described in U.S. patent application Ser. No. 11/009,298, filed on Dec. 10, 2004 (now U.S. Pat. No. 7,091,231 issued Aug. 15, 2006), FIG. 6.

3-[3-((1R,2S,3R,5R)-5-Chloro-3-hydroxy-2-{3-[hydroxy-(1-propyl-cyclobutyl)-methyl]-phenyl}-cyclopentylmethyl)-phenyl]-propionic acid methyl ester and 3-[3-((1R,2S,3R,5R)-5-Chloro-3-hydroxy-2-{3-[hydroxy-(1-propyl-cyclobutyl)-methyl]-phenyl}-cyclopentylmethyl)-phenyl]-propionic acid (entry 4, table 1). The title compounds were prepared similarly to 3-4/3-5 starting with aryl bromide 3-6 (prepared as described in U.S. patent application Ser. No. 11/009,298, filed on Dec. 10, 2004 (now U.S. Pat. No. 7,091, 231 issued Aug. 15, 2006) FIGS. 1,4).

(2R,3S,4R)-2-Allyl-4-(tert-butyl-dimethyl-silanyloxy)-3-{4-[1-(tert-butyl-dimethyl-silanyloxy)-hexyl]-phenyl}

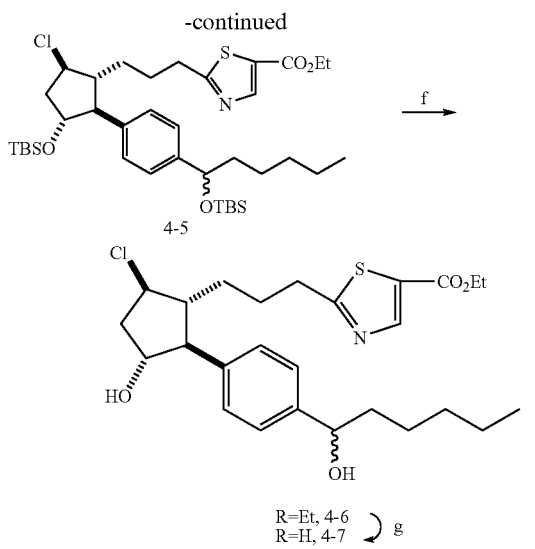

R=Et, 4-6
R=H, 4-7 } g (a) t-BuLi; Me₂Zn; (b) allyl bromide, HMPA; (c) L-selectride; (d) MsCl, TEA; TBAC 40 °C.; (e) 9-BBN; PdCl₂(dppf), K₃PO₄, DMF 50 °C.; (f) HF·pyridine 0 °C.; (g) aq.LiOH, THF.

cyclopentanone (4-1). Compound 4-1 was prepared using an analogous procedure to that described for 3-1.

4-1→(1S,2R,3S,4R)-2-Allyl-4-(tert-butyl-dimethyl-silanyloxy)-3-{4-[1-(tert-butyl-dimethyl-silanyloxy)-hexyl]-phenyl}-cyclopentanol (4-2)→1-[(1S,2R,3R,5R)-2-Allyl-5-(tert-butyl-dimethyl-silanyloxy)-3-chloro-cyclopentyl]-4-[1-(tert-butyl-dimethyl-silanyloxy)-hexyl]-benzene (4-3). This sequence was performed as described in U.S. patent application Ser. No. 11/009,298, filed on Dec. 10, 2004 (now U.S. Pat. No. 7,091,231 issued Aug. 15, 2006), FIG. 6.

2-[3-((1R,2S,3R,5R)-3-(tert-Butyl-dimethyl-silanyloxy)-2-{4-[1-(tert-butyl-dimethyl-silanyloxy)-hexyl]-phenyl}-5-chloro-cyclopentyl)-propyl]-thiazole-5-carboxylic acid ethyl ester (4-5). A solution of 4-3 (39 mg, 0.069 mmol) in 0.2 mL THF was cannula transferred to a mixture of 9-BBN dimer (17 mg, 0.07 mmol) in 0.2 mL THF, rinsing with 0.2 mL THF. The reaction was placed in a 50° C. oil bath for 2.5 h, was allowed to cool to room temperature and H₂O (10 μL) was added. After 30 min., the solution was cannula transferred to a solution of ethyl 2-bromothiazole-5-carboxylate 4-4 (15 mg, 0.063 mmol) and PdCl₂(dppf) (5 mg, 0.007 mmol) in DMF (0.2 mL). K₃PO₄ (31 μL, 0.09 mmol, 3 M) was added and the solution was placed in a 50° C. oil bath. The reaction was stirred overnight and then partitioned between 15 mL ethyl acetate/15 mL water (a little brine was added). The aqueous layer was further extracted with 15 mL ethyl acetate and the combined ethyl acetate solution was dried (MgSO₄), filtered and evaporated. Purification by preparative TLC on silica gel (10% ethyl acetate/hexanes) gave the title compound (4 mg, 0.0057 mmol, 8%).

4-5→2-(3-{(1R,2S,3R,5R)-5-Chloro-3-hydroxy-2-[4-(1-hydroxy-hexyl)-phenyl]-cyclopentyl}-propyl)-thiazole-5-carboxylic acid ethyl ester (4-6)→2-(3-{(1R,2S,3R,5R)-5-Chloro-3-hydroxy-2-[4-(1-hydroxy-hexyl)-phenyl]-cyclopentyl}-propyl)-thiazole-5-carboxylic acid (4-7). This sequence was performed as described in U.S. patent application Ser. No. 11/009,298, filed on Dec. 10, 2004 (now U.S. Pat. No. 7,091,231 issued Aug. 15, 2006), FIG. 6.

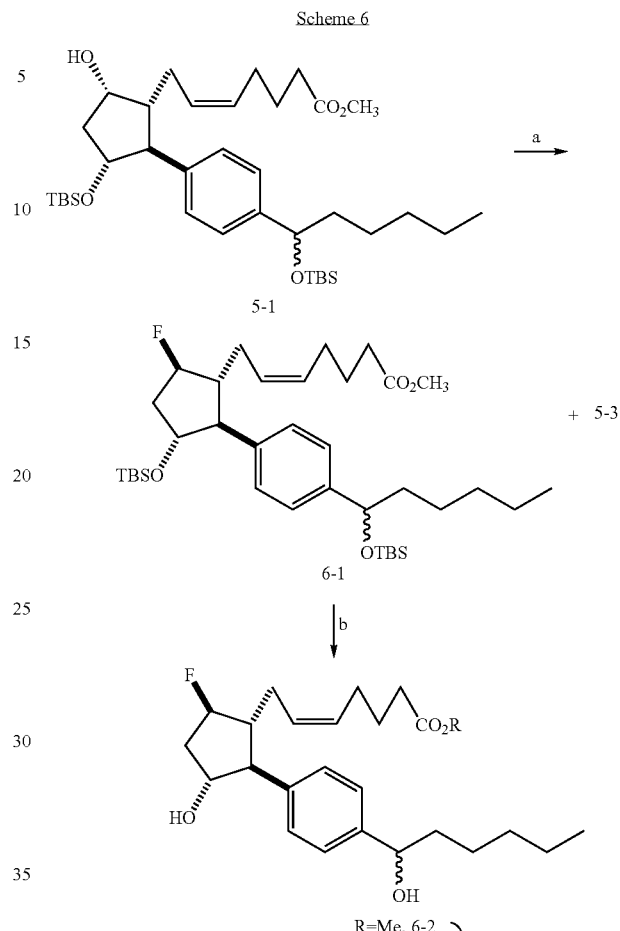

Scheme 6

R=Me, 6-2
R=H, 6-3 } c (a) MsCl, TEA; NaCN, DMSO 80 °; (b) HF-pyridine, 0 °C.; (c) aq.LiOH, THF.

(Z)-7-((1R,2S,3R,5R)-3-(tert-Butyl-dimethyl-silanyloxy)-2-{4-[1-(tert-butyl-dimethyl-silanyloxy)-hexyl]-phenyl}-5-fluoro-cyclopentyl)-hept-5-enoic acid methyl ester (6-1). A solution of 5-1 (109 mg, 0.17 mmol) in 0.5 mL dichloromethane was cannula transferred to a −78° C. solution of deoxofluor [bis(2-methoxyethyl)aminosulfur trifluoride, 34 μL, 0.18 mmol) in 0.75 mL dichloromethane, rinsing with 0.25 mL dichloromethane. The reaction was stirred for 2 h at −78° C. and then was quenched by addition of 10 mL saturated NaHCO₃. The mixture was extracted with dichloromethane (3×15 mL) and the combined dichloromethane solution was dried (MgSO₄), filtered and evaporated. Purification by flash chromatography on silica gel (1% ethyl acetate/hexanes→2%) gave 25 mg (23%) of 5-3 and 53 mg of impure 6-1.

(Z)-7-{(1R,2S,3R,5R)-5-Fluoro-3-hydroxy-2-[4-(1-hydroxy-hexyl)-phenyl]-cyclopentyl}-hept-5-enoic acid methyl ester (6-2). The HF-pyridine procedure described in U.S. patent application Ser. No. 11/009,298, filed on Dec. 10, 2004 (now U.S. Pat. No. 7,091,231 issued Aug. 15, 2006) was followed, which gave 30 mg of impure 6-2 after flash chromatography on silica gel (40% ethyl acetate/hexanes). Further purification by preparative TLC (35% ethyl acetate/hexanes) gave 7 mg of pure 6-2.

(Z)-7-{(1R,2S,3R,5R)-5-Fluoro-3-hydroxy-2-[4-(1-hydroxy-hexyl)-phenyl]-cyclopentyl}-hept-5-enoic acid (6-3). The previously described LiOH procedure was used (U.S. patent application Ser. No. 11/009,298, filed on Dec. 10, 2004, now U.S. Pat. No. 7,091,231 issued Aug. 15, 2006).

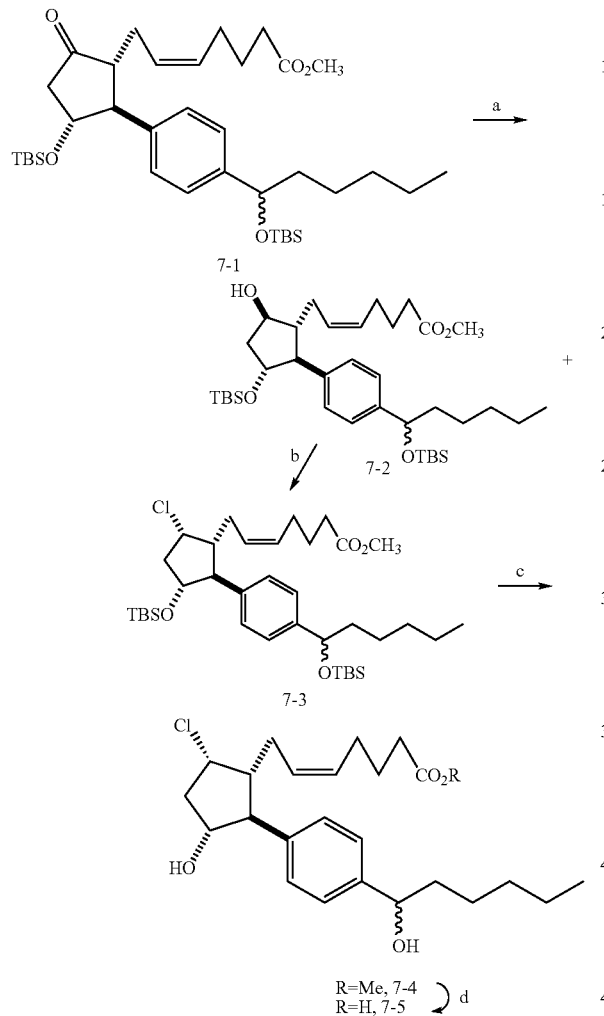

(a) NaBH4; (b) MsCl, TEA; TBAC 80 °C.; (c) HF•pyridine, 0 °C.; (d) rabbit liver esterase.

(Z)-7-((1R,2S,3R,5S)-3-(tert-Butyl-dimethyl-silanyloxy)-2-{4-[1-(tert-butyl-dimethyl-silanyloxy)-hexyl]-phenyl}-5-hydroxy-cyclopentyl)-hept-5-enoic acid methyl ester (5-1) and (Z)-7-((1R,2S,3R,5R)-3-(tert-Butyl-dimethyl-silanyloxy)-2-{4-[1-(tert-butyl-dimethyl-silanyloxy)-hexyl]-phenyl}-5-hydroxy-cyclopentyl)-hept-5-enoic acid methyl ester (7-2). NaBH$_4$ (9 mg, 0.24 mmol) was added to a solution of (Z)-7-((1R,2S,3R)-3-(tert-Butyl-dimethyl-silanyloxy)-2-{4-[1-(tert-butyl-dimethyl-silanyloxy)-hexyl]-phenyl}-5-oxo-cyclopentyl)-hept-5-enoic acid methyl ester (7-1) (55 mg, 0.087 mmol, prepared as described in U.S. patent application Ser. No. 11/009,298, filed on Dec. 10, 2004, (now U.S. Pat. No. 7,091,231 issued Aug. 15, 2006, FIG. 5) in methanol (0.5 mL). After 20 min., 1 M HCl (10 mL) was added and the resulting mixture was extracted with dichloromethane (3×10 mL). The combined dichloromethane solution was dried (MgSO$_4$), filtered and evaporated. Purification by flash chromatography on silica gel (10% ethyl acetate/hexanes→15%) gave 27 mg (49%) of 7-2 and 16 mg (29%) of 5-1 along with an 8 mg mixed fraction.

(Z)-7-((1R,2S,3R,5S)-3-(tert-Butyl-dimethyl-silanyloxy)-2-{4-[1-(tert-butyl-dimethyl-silanyloxy)-hexyl]-phenyl}-5-chloro-cyclopentyl)-hept-5-enoic acid methyl ester (7-3). Methanesulfonyl chloride (15 µL, 0.19 mmol) and triethylamine (30 µL, 0.21 mmol) were added to a solution of 7-2 (50 mg, 0.08 mmol) in dichloromethane (0.3 mL). After 1.5 h, saturated sodium bicarbonate solution (15 mL) was added and the resulting mixture was extracted with dichloromethane (3×15 mL). The combined dichloromethane solution was evaporated to give the crude mesylate.

The crude mesylate was taken into 0.7 mL toluene and (n-Bu)$_4$NCl (246 mg, 0.90 mmol) was added. The mixture was stirred at 80° C. for 1 h and then was filtered through silica gel (20% ethyl acetate/hexanes) to give 7-3 (40 mg, 77%).

7-3→(Z)-7-{(1R,2S,3R,5S)-5-Chloro-3-hydroxy-2-[4-(1-hydroxy-hexyl)-phenyl]-cyclopentyl}-hept-5-enoic acid methyl ester (7-4)→(Z)-7-{(1R,2S,3R,5S)-5-Chloro-3-hydroxy-2-[4-(1-hydroxy-hexyl)-phenyl]-cyclopentyl}-hept-5-enoic acid (7-5). This sequence was completed as shown in scheme 7, following procedures described in U.S. patent application Ser. No. 11/009,298, filed on Dec. 10, 2004 (now U.S. Pat. No. 7,091,231 issued Aug. 15, 2006).

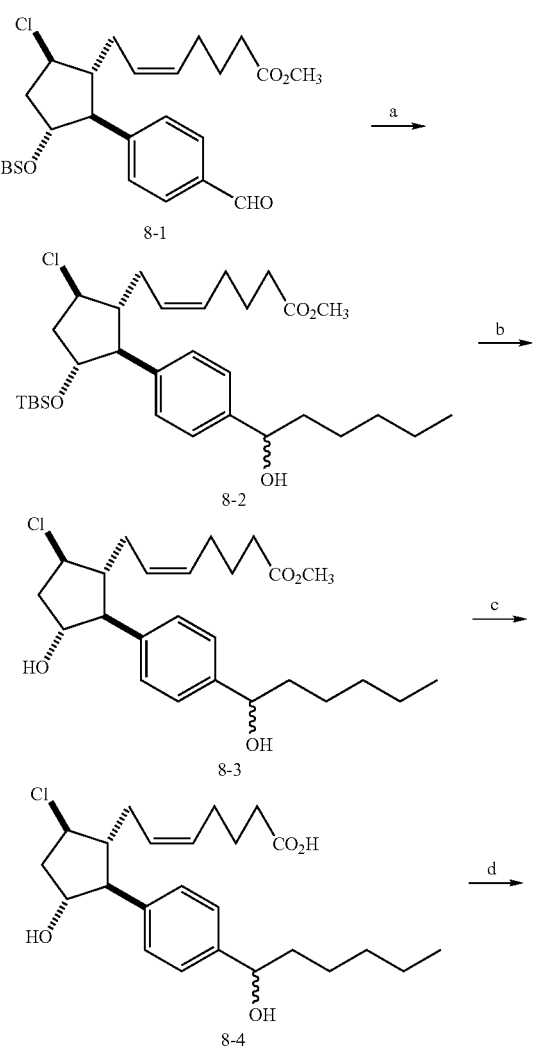

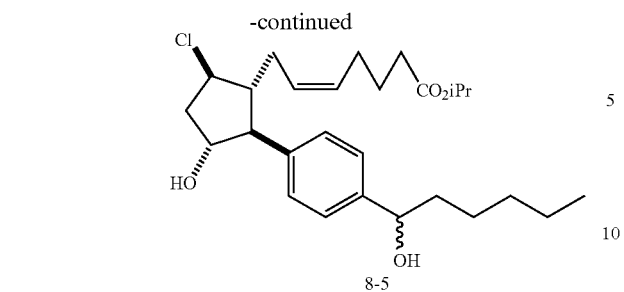

(a) n-pentylMgBr; (b) HF-pyridine 0 °C.; (c) 1 M LiOH, THF; (d) 2-iodopropane, DBU, acetone.

(Z)-7-{(1R,2S,3R,5R)-5-Chloro-3-hydroxy-2-[4-(1-hydroxy-hexyl)-phenyl]-cyclopentyl}-hept-5-enoic acid (8-4). The title compound was prepared as shown in scheme 8, in a similar manner to that described in U.S. patent application Ser. No. 11/009,298, filed on Dec. 10, 2004, (now U.S. Pat. No. 7,091,231 issued Aug. 15, 2006), FIG. 9.

(Z)-7-{(1R,2S,3R,5R)-5-Chloro-3-hydroxy-2-[4-(1-hydroxy-hexyl)-phenyl]-cyclopentyl}-hept-5-enoic acid isopropyl ester (8-5). The title compound was prepared using the standard procedure described in U.S. patent application Ser. No. 11/009,298, filed on Dec. 10, 2004 (now U.S. Pat. No. 7,091,231 issued Aug. 15, 2006).

Preparation of the individual diastereomers of 8-4 (entries 12 and 13, table 1). The individual diastereomers were separated by preparative HPLC at the stage of 8-2: ca. 5 mg sample/run; Chiralcel OD semiprep column (1×25 cm), 2.4 mL/min. flow rate, 10% isopropyl alcohol/hexanes; retention times=17.6 min. and 23.8 min. The individual diastereomers were then taken on separately as shown in scheme 8 and as described in U.S. patent application Ser. No. 11/009,298, filed on Dec. 10, 2004 (now U.S. Pat. No. 7,091,231 issued Aug. 15, 2006).

Compounds contained in entries 15-30, table 1. These compounds were prepared in an analogous fashion to 8-4 (scheme 8).

Scheme 9

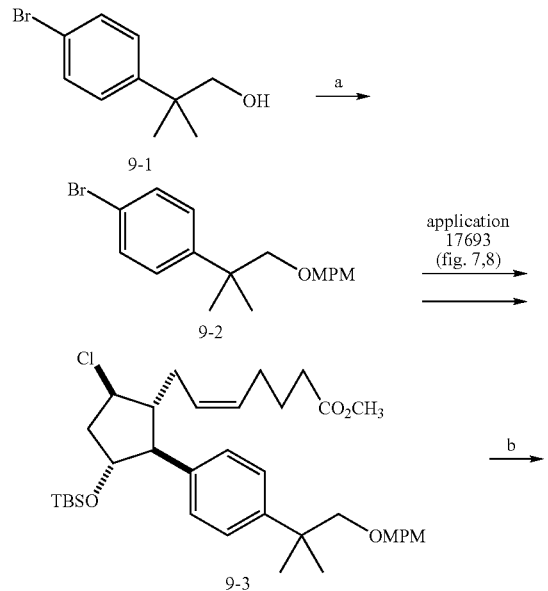

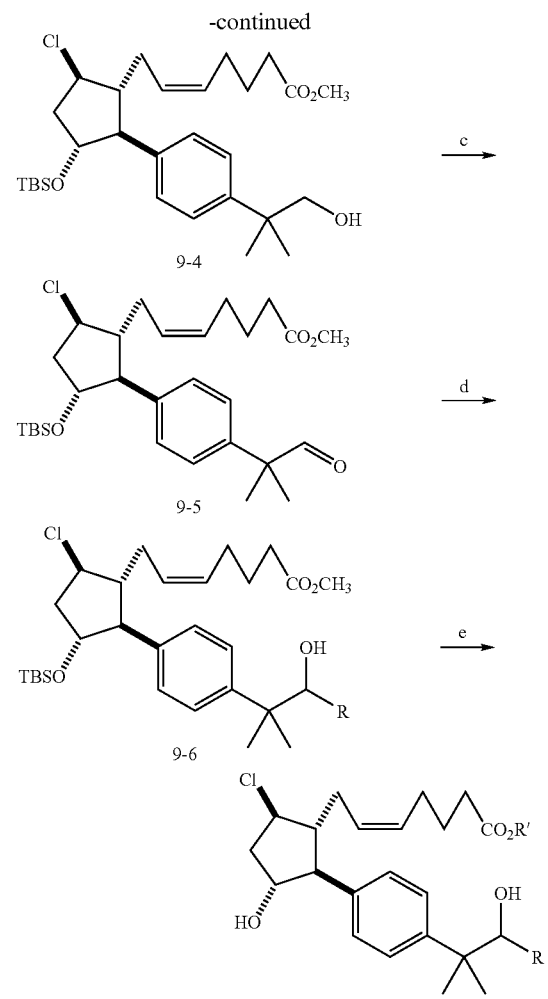

(a) 4-methoxybenzyl chloride, NaH; (b) DDQ; (c) TPAP, NMO; (d) RMgX; (e) HF-pyridine 0 °C.; (f) 1 M LiOH, THF; (g) 2-iodopropane, DBU, acetone.

(Z)-7-{(1R,2S,3R,5R)-5-Chloro-3-hydroxy-2-[4-(2-hydroxy-1,1-dimethyl-heptyl)-phenyl]-cyclopentyl}-hept-5-enoic acid (entry 31, table 1) and (Z)-7-{(1R,2S,3R,5R)-5-Chloro-3-hydroxy-2-[4-(2-hydroxy-1,1-dimethyl-hexyl)-phenyl]-cyclopentyl}-hept-5-enoic acid (entry 32, table 1). The title compounds were prepared as shown in scheme 9, using analogous procedures to those described in U.S. patent application Ser. No. 11/009,298, filed on Dec. 10, 2004 (now U.S. Pat. No. 7,091,231 issued Aug. 15, 2006), FIGS. 7-9.

Scheme 10

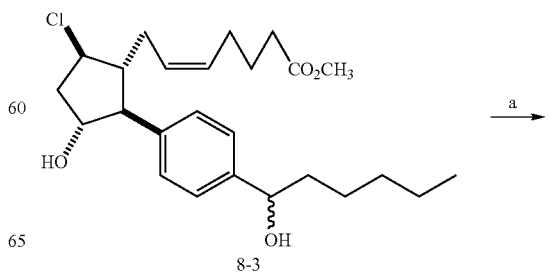

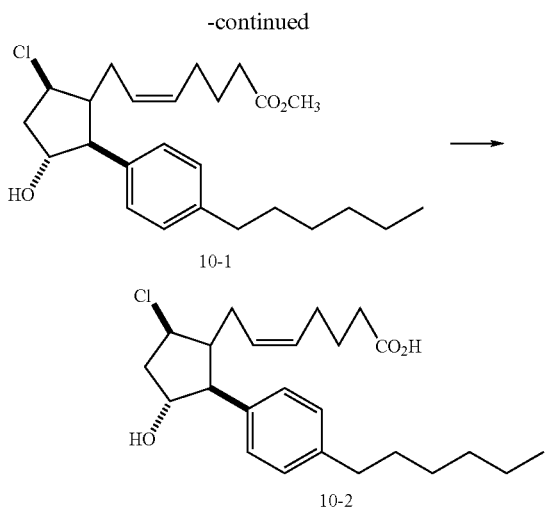

(a) Et₃SiH, TFA, ClCH₂CH₂Cl; (b) aq. LiOH, THF.

(Z)-7-[(1R,2S,3R,5R)-5-Chloro-2-(4-hexyl-phenyl)-3-hydroxy-cyclopentyl]-hept-5-enoic acid methyl ester (10-1). Et₃SiH (30 μL, 0.19 mmol) followed by TFA (90 μL, 1.17 mmol) were added to a solution of 8-3 (23 mg, 0.046 mmol) in dichloroethane (0.10 mL). After 15 min., the reaction was quenched by addition of 4 mL saturated sodium bicarbonate solution. The resulting mixture was extracted with dichloromethane (3×30 mL) and the combined dichloromethane solution was dried (Na₂SO₄), filtered and evaporated. Purification by flash chromatography on silica gel (10% ethyl acetate/hexanes→15%→20%) gave 21 mg (110%) of 10-1.

(Z)-7-[(1R,2S,3R,5R)-5-Chloro-2-(4-hexyl-phenyl)-3-hydroxy-cyclopentyl]-hept-5-enoic acid (10-2). The title compound was prepared using the standard LiOH procedure described in U.S. patent application Ser. No. 11/009,298, filed on Dec. 10, 2004 (now U.S. Pat. No. 7,091,231 issued Aug. 15, 2006).

Scheme 11

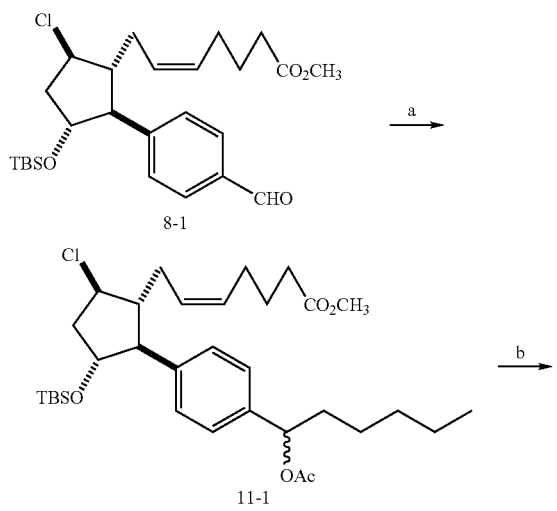

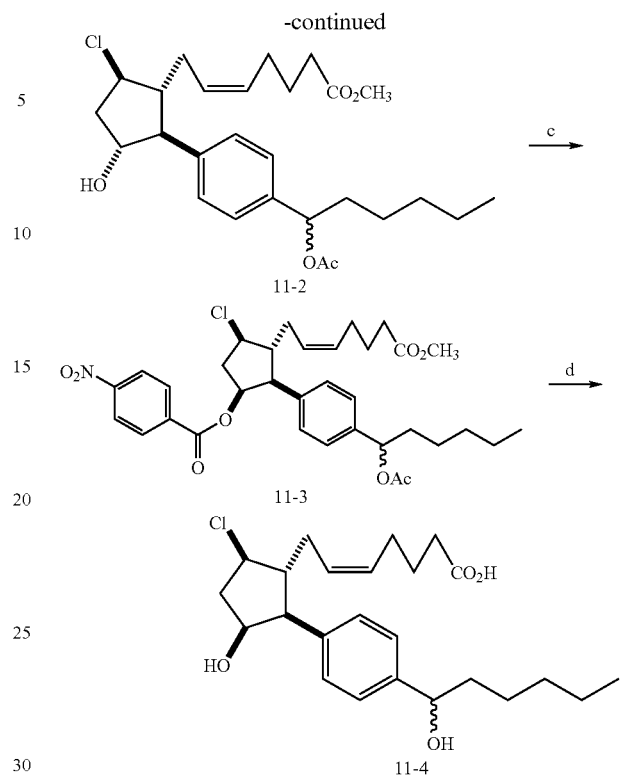

(a) n-pentylMgBr; EtOAc; (b) HF-pyridine 0 °C.; (c) Ph₃P, diisopropyl azodicarboxylate, 4-nitrobenzoic acid, THF; (d) 1 M LiOH, THF.

(Z)-7-[(1R,2S,3R,5R)-2-[4-(1-Acetoxy-hexyl)-phenyl]-3-(tert-butyl-dimethyl-silanyloxy)-5-chloro-cyclopentyl]-hept-5-enoic acid methyl ester (11-1). n-PentylMgBr (130 μL, 0.26 mmol) was added to a 0° C. solution of 8-1 (114 mg, 0.24 mmol) in THF (0.9 mL). After 2.5 h, 1 mL ethyl acetate was added and the reaction was allowed to warm to room temperature. After 30 min. at room temperature, 10 mL saturated ammonium chloride solution was added and the resulting mixture was extracted with ethyl acetate (3×30 mL). The combined ethyl acetate solution was dried (Na₂SO₄), filtered and evaporated. Purification by flash chromatography on silica gel (10% ethyl acetate/hexanes) gave 113 mg (80%) of 11-1.

(Z)-7-{(1R,2S,3R,5R)-2-[4-(1-Acetoxy-hexyl)-phenyl]-5-chloro-3-hydroxy-cyclopentyl}-hept-5-enoic acid methyl ester (11-2). The standard HF.pyridine deprotection described in U.S. patent application Ser. No. 11/009,298, filed on Dec. 10, 2004 (now U.S. Pat. No. 7,091,231 issued Aug. 15, 2006) was used.

4-Nitro-benzoic acid (1S,2S,3R,4R)-2-[4-(1-acetoxy-hexyl)-phenyl]-4-chloro-3-((Z)-6-methoxycarbonyl-hex-2-enyl)-cyclopentyl ester (11-3). Diisopropyl azodicarboxylate (11 μL, 0.057 mmol) was added to a mixture of Ph₃P (15.6 mg, 0.059 mmol), 4-nitrobenzoic acid (8.3 mg, 0.050 mmol), and 11-2 (17 mg, 0.036 mmol) in THF (0.600 mL). The reaction was stirred overnight and then the volatiles were evaporated in vacuo. Purification of the residue by flash chromatography on silica gel (30% ethyl acetate/hexanes) gave 10 mg (45%) of 11-3.

(Z)-7-{(1R,2S,3S,5R)-5-Chloro-3-hydroxy-2-[4-(1-hydroxy-hexyl)-phenyl]-cyclopentyl}-hept-5-enoic acid (11-4). The standard LiOH hydrolysis procedure described in U.S. patent application Ser. No. 11/009,298, filed on Dec. 10, 2004 (now U.S. Pat. No. 7,091,231 issued Aug. 15, 2006) was used.

EXAMPLE 2

Binding Data

Ki

Competition binding experiments were performed in a medium containing Hank's balanced salt solution, Hepes 20 mM, pH 7.3, membranes (~60 µg protein) or 2×10$^5$ cells from HEK 293 cells stably expressing human EP2 receptors, [$^3$H] PGE2 (10 nM) and various concentrations of test compounds in a total volume of 300 µl. Reaction mixtures were incubated at 23° C. for 60 min, and were filtered over Whatman GF/B filters under vacuum. Filters were washed three times with 5 ml ice-cold buffer containing 50 mM Tris/HCl (pH 7.3). Non-specific binding was estimated in the presence of excess unlabeled PGE2 (10 µM). Binding data fitted to the binding model for a single class of binding sites, using nonlinear regression analysis. IC$_{50}$ values thus obtained were converted to Ki using the equation of Ki=(IC$_{50}$/(1+[L]/K$_D$) where [L] represents PGE2 concentration (10 nM) and K$_D$ the dissociation constant for [$^3$H]PGE2 at human EP2 receptors (40 nM).

Radioligand Binding

Cells Stably Expressing EP$_1$, EP$_2$, EP$_4$ and FP Receptors

HEK-293 cells stably expressing the human or feline FP receptor, or EP$_1$, EP$_2$, or EP$_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM MgCl$_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-] 17-phenyl PGF$_{2\alpha}$ (5 nM) were performed in a 100 µl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H-] PGE$_2$ (specific activity 180 Ci mmol) was used as the radioligand for EP receptors. [$^3$H] 17-phenyl PGF$_{2\alpha}$ was employed for FP receptor binding studies. Binding studies employing EP$_1$, EP$_2$, EP$_4$ and FP receptors were performed in duplicate in at least three separate experiments. A 200 µl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-PGE$_2$, or 5 nM [$^3$H] 17-phenyl PGF$_{2\alpha}$, and non-specific binding determined with 10$^{-5}$M of unlabeled PGE$_2$, or 17-phenyl PGF$_{2\alpha}$, according to receptor subtype studied.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; hEP$_1$; hEP$_2$/Gqs5; hEP$_{3,4}$/Gqi5; hEP$_4$/Gqs5; hFP; hIP; hTP), were cultured in 100 mm culture dishes in high-glucose DMEM medium containing 10% fetal bovine serum, 2 mM l-glutamine, 250 µg/ml geneticin (G418) and 200 µg/ml hygromycin B as selection markers, and 100 units/ml penicillin G, 100 µg/ml streptomycin and 0.25 µg/ml amphotericin B.

(b) Calcium Signal Studies on the FLIPR™

Cells were seeded at a density of 5×10$^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates were washed four times with HBSS-HEPES buffer to remove excess dye leaving 100 µl in each well. Plates were re-equilibrated to 37° C. for a few minutes.

Cells were excited with an Argon laser at 488 nm, and emission was measured through a 510-570 nm bandwidth emission filter (FLIPR™, Molecular Devices, Sunnyvale, Calif.). Drug solution was added in a 50 µl volume to each well to give the desired final concentration. The peak increase in fluorescence intensity was recorded for each well. On each plate, four wells each served as negative (HBSS-HEPES buffer) and positive controls (standard agonists: BW245C (hDP); PGE$_2$ (hEP$_1$; hEP$_2$/Gqs5; hEP$_{3,4}$/Gqi5; hEP$_4$/Gqs5); PGF$_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of 10$^{-5}$ M. To generate concentration-response curves, four compounds per plate were tested in duplicates in a concentration range between 10$^{-5}$ and 10$^{-11}$ M. The duplicate values were averaged. In either, HTS or CoRe format each compound was tested on at least 3 separate plates using cells from different passages to give an n≧3.

cAMP Assay

A 384-well drug plate was prepared to contain 6 test compounds, PGE2 and cAMP in 16 serial dilutions in triplicate, using a Biomek station. HEK-EBNA cells expressing a target PG receptor subtype (EP2 or EP4) were suspended in a stimulation buffer (HBSS, 0.1% BSA, 0.5 mM IBMX and 5 mM HEPES, pH 7.4) in a density of 10$^4$ cells/5 µl. The reaction was initiated by mixing 5 µL drug dilutions with 5 µl of HEK-EBNA cells in a well, carried out for 30 min at room temperature, and followed by the addition of 5 µl anti-cAMP acceptor beads in the control buffer with Tween-20 (25 mM NaCl, 0.03% Tween-20, 5 mM HEPES, pH7.4). After 30 min in the dark at room temperature, the mixtures were incubated with 15 µl biotinylated-cAMP/strepavidin donor beads in Lysis/Detection buffer (0.1% BSA, 0.3% Tween-20 and 5 mM HEPES, pH7.4) for 45 min at the room temperature. Fluorescence changes were read using a Fusion-alpha HT microplate reader.

The results of the binding and activity studies, presented in Table 1 below, demonstrate that the compounds disclosed herein are selective prostaglandin EP$_2$ agonists, and are thus useful for the treatment of glaucoma, ocular hypertension, the other diseases or conditions disclosed herein.

TABLE 1

| ENTRY | STRUCTURE[a] | BINDING-Ki (nM) | | Ca²⁺ Signal-EC50 (nM)[b] | | | | | | | |
|---|---|---|---|---|---|---|---|---|---|---|---|
| | | EP2 | EP4 | FP | EP1 | EP2 | EP3 | EP4 | TP | IP | DP |
| 1 | *structure* | | | not active | 917 | 2446 | 4152 | not active | not active | not active | not active |
| 2 | *structure* | 24 | 3018 | not active | 664 | 4 (2) | 348 | not active | not active | not active | not active |
| 3 | *structure* | 2779 | 3950 | not active | not active | 158 (56) | 4674 | | not active | not active | not active |
| 4 | *structure* | >10 K | >10 K | not active | not active | 4111 (69) | not active | >10 K | not active | not active | not active |
| 5 | *structure* | 6175 | | not active | not active | 619 (1065) | not active | >10 K | not active | not active | not active |

TABLE 1-continued

| EN-TRY | STRUCTURE[a] | BINDING-Ki (nM) | | Ca$^{2+}$ Signal-EC50 (nM)[b] | | | | | | | |
|---|---|---|---|---|---|---|---|---|---|---|---|
| | | EP2 | EP4 | FP | EP1 | EP2 | EP3 | EP4 | TP | IP | DP |
| 8 | | 804 | >10 K | not active | not active | 53 (8) | 1451 | not active | not active | 10061 | not active |
| 9 | | 3951 | 4586 | not active | not active | 242 (324) | 7235 | 947 | not active | 6882 | not active |
| 10 | | not active | not active | 3956 | not active | not active | not active | not active | not active | not active | not active |

TABLE 1-continued

| EN-TRY | STRUCTURE[a] | BINDING-Ki (nM) | | Ca$^{2+}$ Signal-EC50 (nM)[b] | | | | | | | |
|---|---|---|---|---|---|---|---|---|---|---|---|
| | | EP2 | EP4 | FP | EP1 | EP2 | EP3 | EP4 | TP | IP | DP |
| 11 | | 209 | >10 K | not active | not active | 7 (3) | 456 | >10 K | not active | not active | not active |
| 12[c] | | 209 | >10 K | not active | not active | 36 (38) | not active | >10 K | not active | not active | not active |
| 13[d] | | 73 | >10 K | not active | not active | 11 (3) | 2999 | >10 K | not active | not active | not active |

TABLE 1-continued

| EN-TRY | STRUCTURE[a] | BINDING-Ki (nM) | | Ca$^{2+}$ Signal-EC50 (nM)[b] | | | | | | | |
|---|---|---|---|---|---|---|---|---|---|---|---|
| | | EP2 | EP4 | FP | EP1 | EP2 | EP3 | EP4 | TP | IP | DP |
| 14 | | 287 | 8612 | not active | not active | 28 (76) | 477 | >10 K | not active | not active | not active |
| 15 | | 260 | 3812 | not active | not active | 495 (176) | 2224 | not active | not active | not active | not active |
| 16 | | 1289 | 5581 | not active | not active | 2334 (5259) | 1708 | not active | not active | not active | not active |

TABLE 1-continued

| EN-TRY | STRUCTURE[a] | BINDING-Ki (nM) | | Ca²⁺ Signal-EC50 (nM)[b] | | | | | | | |
|---|---|---|---|---|---|---|---|---|---|---|---|
| | | EP2 | EP4 | FP | EP1 | EP2 | EP3 | EP4 | TP | IP | DP |
| 17 | [structure: chlorocyclopentane with hydroxyl, pendant phenyl-CH(OH)-CH2-cyclohexyl, and Z-pentenoic acid chain] | 483 | 15922 | not active | not active | 953 (495) | not active | not active | not active | not active | not active |
| 18 | [structure: chlorocyclopentane with hydroxyl, pendant phenyl-CH(OH)-CH2-cyclohexyl, and Z-hexenoic acid chain] | 2287 | 4940 | not active | not active | 2254 (2660) | not active | >10 K | not active | not active | not active |
| 19 | [structure: chlorocyclopentane with hydroxyl, pendant phenyl-CH(OH)-(CH2)3-C(CH3)3, and Z-pentenoic acid chain] | 1053 | 6287 | | | >10 K (815) | | >10 K | | | |

TABLE 1-continued
| EN-TRY | STRUCTURE[a] | BINDING-Ki (nM) | | Ca$^{2+}$ Signal-EC50 (nM)[b] | | | | | | | |
|---|---|---|---|---|---|---|---|---|---|---|---|
| | | EP2 | EP4 | FP | EP1 | EP2 | EP3 | EP4 | TP | IP | DP |
| 20 | 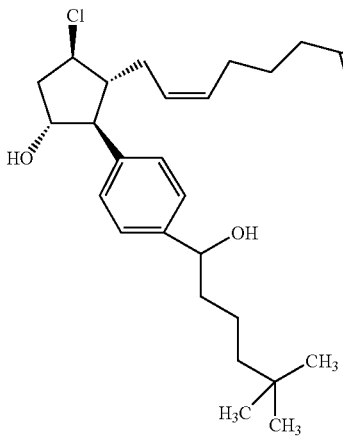 | 3849 | 3805 | not active | not active | 5394 (>10 K) | 4449 | 10725 | not active | not active | not active |
| 21 | 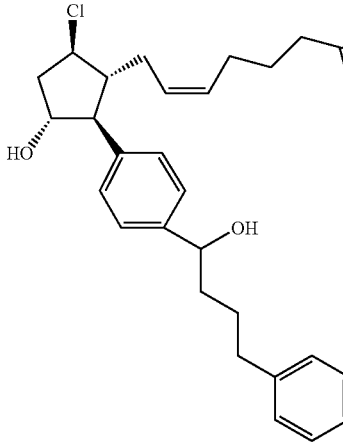 | 77 | >10 K | not active | not active | 9 (14) | not active | >10 K | not active | not active | not active |
| 22 | 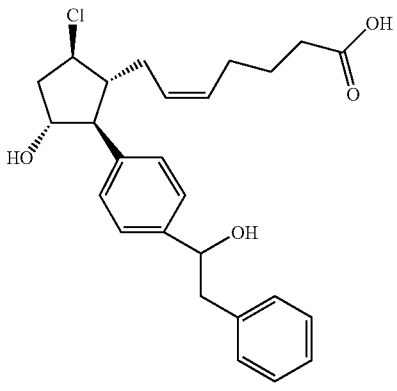 | 148 | >10 K | not active | not active | 51 (59) | not active | 15806 | not active | not active | not active |

TABLE 1-continued

| EN-TRY | STRUCTUREa | BINDING-Ki (nM) | | Ca$^{2+}$ Signal-EC50 (nM)b | | | | | | | |
|---|---|---|---|---|---|---|---|---|---|---|---|
| | | EP2 | EP4 | FP | EP1 | EP2 | EP3 | EP4 | TP | IP | DP |
| 23 | | 1128 | >10 K | not active | not active | 548 (125) | 13712 | >10 K | not active | not active | not active |
| 24 | | 2162 | >10 K | not active | 4523 | 735 (628) | 8826 | >10 K | not active | not active | not active |
| 25 | | 278 | 2263 | not active | not active | 58 (12) | 5932 | not active | not active | not active | not active |

TABLE 1-continued

| EN-TRY | STRUCTURE[a] | BINDING-Ki (nM) | | $Ca^{2+}$ Signal-EC50 (nM)[b] | | | | | | | |
|---|---|---|---|---|---|---|---|---|---|---|---|
| | | EP2 | EP4 | FP | EP1 | EP2 | EP3 | EP4 | TP | IP | DP |
| 26 | | 1657 | >10 K | not active | not active | 154 (7) | not active | not active | not active | not active | not active |
| 27 | | 589 | | not active | not active | (10) | not active | not active | not active | not active | not active |
| 28 | | 564 | | not active | not active | not active | 142 (9) | not active | not active | not active | 1647 |

TABLE 1-continued

| ENTRY | STRUCTURE[a] | BINDING-Ki (nM) | | Ca$^{2+}$ Signal-EC50 (nM)[b] | | | | | | | |
|---|---|---|---|---|---|---|---|---|---|---|---|
| | | EP2 | EP4 | FP | EP1 | EP2 | EP3 | EP4 | TP | IP | DP |
| 29 | | 1388 | >10 K | not active | not active | 119 (38) | 37 | not active | not active | 8489 | not active |
| 30 | | 1255 | >10 K | not active | not active | 68 (10) | 23 | not active | 3747 | 2059 | not active |
| 31 | | 182 | 5406 | not active | not active | 544 (19) | 1301 | not active | not active | not active | not active |

TABLE 1-continued

| ENTRY | STRUCTURE[a] | BINDING-Ki (nM) | | Ca$^{2+}$ Signal-EC50 (nM)[b] | | | | | | | |
|---|---|---|---|---|---|---|---|---|---|---|---|
| | | EP2 | EP4 | FP | EP1 | EP2 | EP3 | EP4 | TP | IP | DP |
| 32 | | 225 | 9636 | not active | not active | 164 (9) | 2811 | not active | not active | not active | not active |
| 33 | | 83 | >10 K | not active | not active | 26 (27) | not active | >10 K | not active | not active | not active |
| 34 | | 12 | | not active | not active | 16 (5) | 25 | not active | 6931 | 3283 | not active |

[a] All compounds are mixtures of diastereomers except where indicated
[b] Data in parentheses refer to measurement of cAMP (see experimental for details)
[c] Faster eluting diastereomer (HPLC); stereochemistry not determined
[d] Slower eluting diastereomer (HPLC); stereochemistry not determined

TABLE 2

| ENTRY | STRUCTURE | Conc. (g/100 mL) | DOG Max. ΔIOP (%) | DOG Max. hyperemia | MONKEY Max. ΔIOP (%) | RABBIT Max. hyperemia |
|---|---|---|---|---|---|---|
| 1[a] | 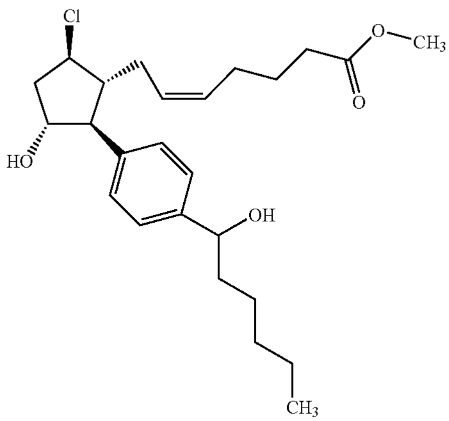 | 0.1% | −50 | 1.5 | | |
| 2[a] | 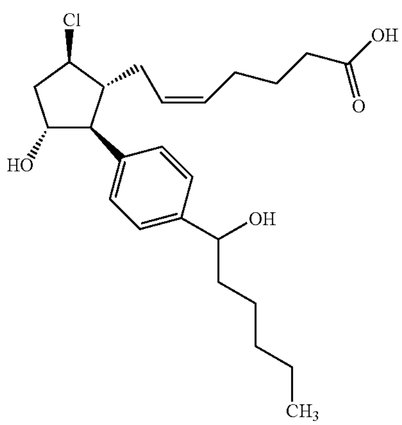 | 0.003% | −21 | 1 | 21 | 0 |
| 3[a] | 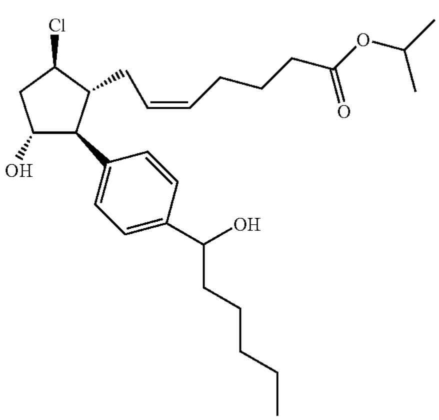 | 0.003% | −33 | 1 | 16 | 0.2 |

TABLE 2-continued

| ENTRY | STRUCTURE | Conc. (g/100 mL) | DOG Max. ΔIOP (%) | Max. hyperemia | MONKEY Max. ΔIOP (%) | RABBIT Max. hyperemia |
|---|---|---|---|---|---|---|
| 4[b] | 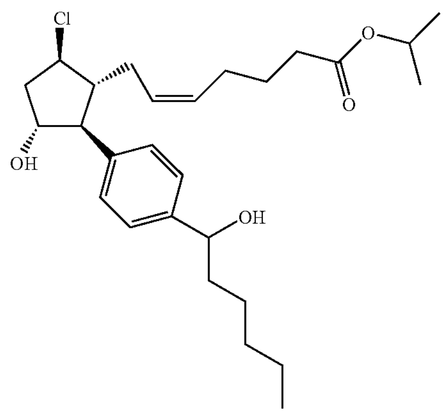 | 0.1% | −13 | 0.5 | 24 | |
| 5[c] | 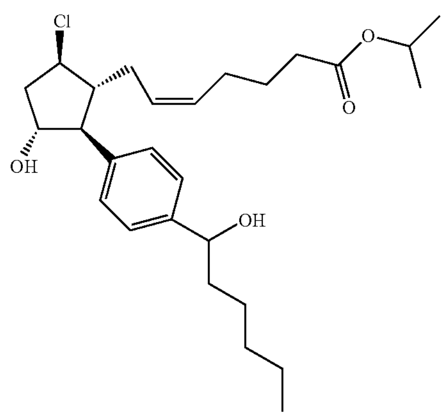 | 0.1% | −47 | 1.5 | 26 | 1.5 |
| 6 | 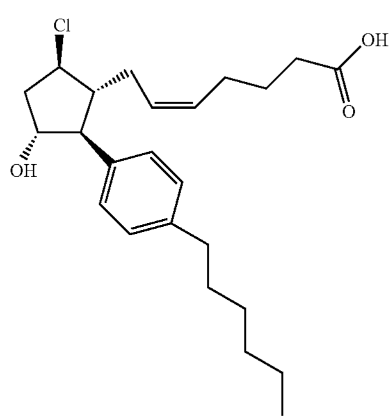 | 0.1% | −43 | 0.6 | 32 | 0.25 |

TABLE 2-continued

| ENTRY | STRUCTURE | Conc. (g/100 mL) | DOG Max. ΔIOP (%) | DOG Max. hyperemia | MONKEY Max. ΔIOP (%) | RABBIT Max. hyperemia |
|---|---|---|---|---|---|---|
| 7 | 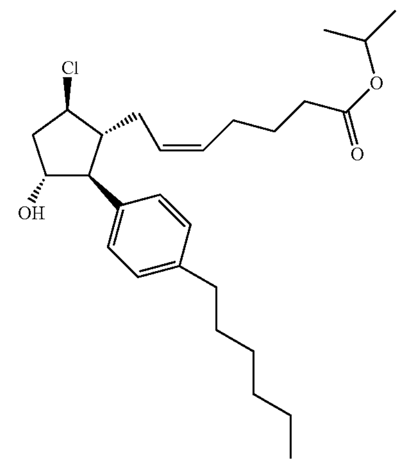 | 0.1 | 20 | 0.5 | 21 | |
| 8 | 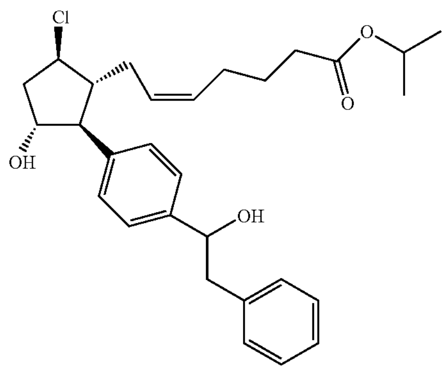 | 0.1% | −40 | 0.8 | 39 | 0 |
| 9 | 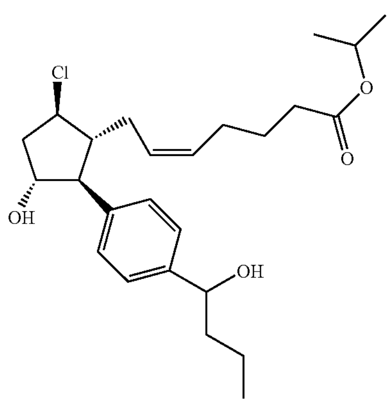 | 0.1% | −36 | 0.5 | 35 | |
| 10 | 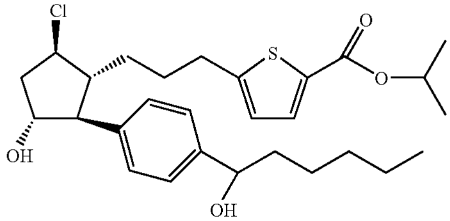 | 0.1 | −50 | 1.8 | | 1 |

($^a$)mixture of diastereomers
($^b$)faster eluting (HPLC) diastereomer
($^c$)slower eluting (HPLC) diastereomer Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in J Pharm Pharmaceut Sci 6 (1): 33-66, 2003 and Shareef et. al (AAPS PharmSci 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid to the colons of humans in clinical trials for the treatment of inflammatory bowel disease. It is also believed that bacteria of the lower GI also have enzymes which can digest glycosides, glucuronides, cyclodextrins, dextrans, and other carbohydrates, and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucouronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, commercially provides pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof, rather, the ambit of the present invention is to be governed only by the lawful construction of the appended claims.

What is claimed is:

1. A compound represented by a formula

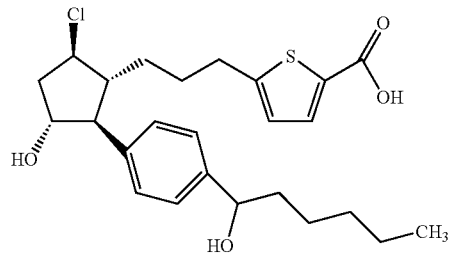

or a pharmaceutically acceptable salt or a prodrug thereof.

2. The compound consisting of

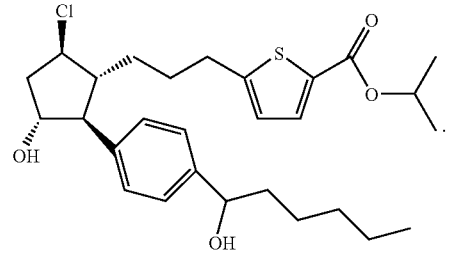

* * * * *